(12) United States Patent
Thayer et al.

(10) Patent No.: US 12,404,536 B2
(45) Date of Patent: *Sep. 2, 2025

(54) DETECTION ASSAY FOR PROTEIN-POLYNUCLEOTIDE CONJUGATES

(71) Applicant: AMGEN INC., Thousand Oaks, CA (US)

(72) Inventors: Mai Thayer, Alameda, CA (US); Sara Humphreys, Oakland, CA (US)

(73) Assignee: AMGEN INC., Thousand Oaks, CA (US)

( * ) Notice: Subject to any disclaimer, the term of this patent is extended or adjusted under 35 U.S.C. 154(b) by 910 days.

This patent is subject to a terminal disclaimer.

(21) Appl. No.: 17/537,378

(22) Filed: Nov. 29, 2021

(65) Prior Publication Data

US 2022/0170074 A1 Jun. 2, 2022

Related U.S. Application Data

(63) Continuation of application No. 16/434,056, filed on Jun. 6, 2019, now Pat. No. 11,208,677.

(60) Provisional application No. 62/681,931, filed on Jun. 7, 2018.

(51) Int. Cl.
*C12Q 1/6804* (2018.01)

(52) U.S. Cl.
CPC .................. *C12Q 1/6804* (2013.01)

(58) Field of Classification Search
CPC .................. C12Q 1/68; C07H 21/00
See application file for complete search history.

(56) References Cited

U.S. PATENT DOCUMENTS

| | | | |
|---|---|---|---|
| 11,208,677 B2 * | 12/2021 | Thayer | C12Q 1/6804 |
| 2003/0032028 A1 | 2/2003 | Dace et al. | |
| 2004/0063922 A1 | 4/2004 | Conrad | |
| 2008/0026388 A1 | 1/2008 | Maxwell | |
| 2008/0050721 A1 | 2/2008 | Radka et al. | |
| 2013/0052731 A1 | 2/2013 | Ma | |

FOREIGN PATENT DOCUMENTS

| | | |
|---|---|---|
| WO | 97/15691 A1 | 5/1997 |
| WO | 99/61071 A2 | 12/1999 |
| WO | 00/29624 A2 | 5/2000 |
| WO | 2008005310 A2 | 1/2008 |
| WO | 2008016680 A1 | 2/2008 |
| WO | 2018039647 A1 | 3/2018 |

OTHER PUBLICATIONS

Ahern H., The Scientist 9(15) : 20 (Year: 1995).*
Cannon et al. Quanitative Molecular Hybridization on Nylon membranes. Analytical Biochemistry 149: 229-237 (Year: 1985).*
Fisher et al.,A System for the Quantitation of DNA Using a Microtiter Plate-Based Hybridization and Enzyme Amplification Technology. Analytical Biochemistry 251: 280 (Year: 1997).*
Jiang et al., mRNA isolation in a microfluidic device for eventual integration of cDNA library construction. Analyst 125: 2176 (Year: 2000).*
Nam et al. Nanoparticle-based bio-bar codes for the ultrasensitive detection of proteins. Sciemce 301 :1884 (Year: 2003).*
Stratagene Catalog, Gene Characterization Kits p. 39 (Year: 1988).*
Ito et al., "Sequence-specific DNA purification by triplex affinity capture," PNAS, vol. 89, pp. 495-498 (1992).
Avino et al. (2012), "Oligonucleotide-peptide conjugates: solid-phase synthesis under acidic conditions and use in ELISA assays", Molecules, 17:13825-13843.
Baumer et al. (2016), "Antibody-coupled siRNA as an efficient method for in vivo mRNA knockdown", Nature Protocols, 11(1):22-36.
Clark et al. (1986), "ELISA techniques", Methods in Enzymol., 118:742-766.
Cuellar et al. (2015), "Systematic evaluation of antibody-mediated siRNA delivery using an industrial platform of THIOMAB-siRNA conjugates", Nucleic Acids Res., 43(2): 1189-1203.
Humphreys et al. (2019), "Quantification of siRNA-antibody conjugates in biological matrices by triplex-forming oligonucleotide ELISA", Nucleic Acid Therap., pp. 1-6.
Karkare and Bhatnagar (2006), "Promising nucleic acid analogs and mimics: characteristic features and applications of PNA, LNA, and morpholino", Appl. Microbiol. Biotechnol., 71:575-586.
Kozlov et al. (2004), "Efficient strategies for the conjugation of oligonucleotides to antibodies enabling highly sensitive protein detection", Biopolymers, 73:621-630.
Patterson et al. (2010), "Using triplex-forming oligonucleotide probes for the reagentless, electrochemical detection of double-stranded DNA", Anal. Chem., 82(21):9109-9115.
Sau et al. (2010), "Invader LNA: efficient targeting of short double stranded DNA", Org. Biomol. Chem., 8:2028-2036.
Sorensen et al. (2004), "Solution structure of a dsDNA:LNA triplex", Nucleic Acids Res., 32(20):1-8.
Tan et al. (2012), "Real-time quantification of antibody-short interfering RNA conjugate in serum by antigen capture reverse transcription-polymerase chain reaction", Analytical Biochem., 430:171-178.
Wang et al. (2016), "Advances in quantitative bioanalysis of oligonucleotide biomarkers and therapeutics", Bioanalysis 8(2): 143.
Wang et al. (2019), "Recent advances in bioanalysis and metabolite profiling of oligonucleotide therapeutics", Bioanalysis Zone.
Wengel et al. (2003), "Chemistry of locked nucleic acids (LNA): design, synthesis, and bio-physical properties", Ltrs. in Peptide Sci., 10:237-253.
Zhou et al. (2013), "Recognition of RNA duplexes by chemically modified triplex-forming oligonucleotides", 41(13):6664-6673.
International Search Report for Application No. PCT/US2019/035888 mailed Aug. 12, 2019.

(Continued)

*Primary Examiner* — Ethan C Whisenant
(74) *Attorney, Agent, or Firm* — Angela L. Purcell

(57) ABSTRACT

The present invention relates to methods for detecting and quantifying intact protein-polynucleotide conjugate molecules in various sample matrices. In particular, the methods utilize triplex forming oligonucleotides in combination with protein-specific binding partners to respectively detect the polynucleotide and protein components of the conjugate molecules.

37 Claims, 11 Drawing Sheets

Specification includes a Sequence Listing.

(56) References Cited

OTHER PUBLICATIONS

Written Opinion for Application No. PCT/US2019/035888 mailed Aug. 12, 2019.
Isogawa et al., "Versatile and efficient chromatin pull-down methodology based on DNA triple helix formation," Scientific Reports, vol. 8(5925), pp. 1-12, Supplementary pp. 1-12 (2018).

* cited by examiner

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(21)
<223> OTHER INFORMATION: Positions 3, 6, 9, 12, 15, 20 LNA monomers

<400> SEQUENCE: 1
aaacttcatc tttcttccca c                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(21)
<223> OTHER INFORMATION: Positions 4, 8, 11, 13, 15, 17, 20 LNA monomers

<400> SEQUENCE: 2
ataaaatcta cagtcatagg a                                            21

<210> SEQ ID NO 3
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(21)
<223> OTHER INFORMATION: Positions 3, 5, 7, 12, 14, 18, 20 LNA monomers

<400> SEQUENCE: 3
aaacttcatc aaacttccca c                                            21

<210> SEQ ID NO 4
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 4

Glu Gln Lys Leu Ile Ser Glu Glu Asp Leu
1               5                   10

<210> SEQ ID NO 5
<211> LENGTH: 9
<212> TYPE: PRT
```

```
<213> ORGANISM: Artificial Sequence
<220> FEATURE:
<223> OTHER INFORMATION: Synthetic polypeptide

<400> SEQUENCE: 5

Tyr Pro Tyr Asp Val Pro Asp Tyr Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 6

Asp Tyr Lys Asp Asp Asp Asp Lys
1               5
```

DETECTION ASSAY FOR PROTEIN-POLYNUCLEOTIDE CONJUGATES

CROSS-REFERENCE TO RELATED APPLICATIONS

This application is a continuation of U.S. application Ser. No. 16/434,056, filed Jun. 6, 2019, which claims the benefit of U.S. Provisional Application No. 62/681,931, filed Jun. 7, 2018, both of which are hereby incorporated by reference in their entireties.

DESCRIPTION OF THE TEXT FILE SUBMITTED ELECTRONICALLY

The present application contains a Sequence Listing, which has been submitted electronically in ASCII format and is hereby incorporated by reference in its entirety. The computer readable format copy of the Sequence Listing, which was created on Nov. 18, 2021, is named A-2248-US-CNT_ST25 and is 1.72 kilobytes in size.

FIELD OF THE INVENTION

The present invention relates to the detection and quantitation of drug conjugate molecules. In particular, the invention relates to methods for detecting and quantitating intact protein-polynucleotide conjugate molecules in a sample using tagged triplex forming oligonucleotides and protein-specific binding partners in sandwich-based assays.

BACKGROUND OF THE INVENTION

Nucleic acid molecules continue to represent a promising class of therapeutics. However, delivery of therapeutic nucleic acid molecules to target tissues has proved to be a challenge and various approaches have been attempted. One such delivery approach entails the conjugation of a therapeutic nucleic acid molecule to a targeting protein that specifically binds to cell surface proteins expressed on the cell types of interest. Thus, these protein-polynucleotide conjugate molecules, such as antibody-siRNA conjugates, are emerging as a new therapeutic modality. As such, it is important to have robust assay methods that enable detection and quantitation of intact protein-polynucleotide conjugate molecules.

Although there are some existing methods that could be adapted to detect intact protein-polynucleotide conjugate molecules, they suffer from several disadvantages. For instance, size exclusion chromatography could be used to separate intact protein-polynucleotide conjugate molecules from other species in solution. However, this method is largely qualitative and requires a high level of sample purity and therefore, is not compatible for use in complex sample matrices, such as serum and tissue homogenates. Other methods, such as sodium dodecyl sulfate polyacrylamide gel electrophoresis (SDS-PAGE), liquid chromatography-mass spectrometry (LC-MS), and nuclear magnetic resonance (NMR), either require conditions that could affect the integrity of the conjugate molecule or various time-consuming steps for sample processing or post-assay data interpretation. Also, none of these methods are compatible with detection or quantitation of the conjugate molecule in complex sample matrices as high purity samples are typically required.

One detection method for antibody-siRNA conjugate molecules utilizing an antigen-based capture step followed by reverse transcription-polymerase chain reaction (RT-PCR) has been reported (Tan et al., Analytical Biochemistry, Vol. 430: 171-178, 2012). However, this method is highly dependent on the efficiency of the PCR primer and probe hybridization, which can be affected by the number and type of chemically-modified nucleotides present in the siRNA molecule. Moreover, the PCR step necessitates the use of high temperatures (e.g. 85° C. or higher), which can result in protein degradation, thereby potentially limiting the use of the assay in more complex sample matrices, such as tissue homogenates.

Thus, there is a need in the art to develop simple assays that enable detection as well as quantitation for intact protein-polynucleotide conjugate molecules across a variety of sample types, including complex biological samples.

SUMMARY OF THE INVENTION

The present invention provides methods for detecting and quantitating protein-polynucleotide conjugate molecules in various sample matrices, including complex biological samples, such as serum and tissue homogenates. In one embodiment, the methods comprise contacting the sample with a triplex forming oligonucleotide (TFO) that is covalently linked to a tag under conditions that allow the TFO to hybridize to the polynucleotide in the conjugate molecule, thereby forming a hybridization mixture; contacting the hybridization mixture with a surface comprising a capture reagent that specifically binds to the tag covalently linked to the TFO; contacting the surface with a detection reagent, wherein the detection reagent comprises a detectable label coupled to a binding partner that specifically binds to the protein in the conjugate molecule; and detecting a signal from the detectable label.

In another embodiment, the methods comprise contacting the sample with a TFO that is covalently linked to a tag under conditions that allow the TFO to hybridize to the polynucleotide in the conjugate molecule, thereby forming a hybridization mixture; contacting the hybridization mixture with a surface comprising a capture reagent that specifically binds to the protein in the conjugate molecule; contacting the surface with a detection reagent, wherein the detection reagent comprises a detectable label coupled to a binding partner that specifically binds to the tag covalently linked to the TFO; and detecting a signal from the detectable label.

The TFO employed in the methods of the invention can have a sequence that is complementary to the sequence of the polynucleotide component of the conjugate molecule. In embodiments in which the polynucleotide component is a double-stranded polynucleotide (e.g. an siRNA), the TFO may have a sequence that is complementary to the sequence of the strand of the polynucleotide that is linked to the protein in the conjugate molecule. In some embodiments, the TFO is at least 15 nucleotides in length and comprises at least one modified nucleotide with a bicyclic sugar modification (e.g. locked nucleic acid). In certain embodiments, the TFO comprises a mixture of locked nucleic acid monomers and deoxyribonucleotides. In such embodiments, about 30% to about 40% of the nucleotides in the TFO are locked nucleic acid monomers. In certain embodiments of the methods of the invention, the TFO is covalently linked to a tag. The tag can be a hapten, such as biotin, digoxigenin, or 2,4-dinitrophenol.

In some embodiments of the methods of the invention, the capture reagent specifically binds to the tag covalently linked to the TFO. In such embodiments, the capture reagent can be an antibody or antigen-binding fragment that specifically binds to the tag. For instance, the tag may be digoxigenin and the capture reagent may be an antibody or antigen-binding fragment that specifically binds to digoxigenin. In other embodiments, the capture reagent is a protein or peptide that specifically binds to the tag. In these embodiments, the tag can be biotin and the capture reagent can be streptavidin.

In other embodiments of the methods of the invention, the capture reagent specifically binds to the protein in the conjugate molecule. In such embodiments, the capture reagent can be an antibody or antigen-binding fragment that specifically binds to the protein in the conjugate molecule. For example, in one embodiment, the protein in the conjugate molecule is an antibody and the capture reagent is an anti-Fc region antibody or an anti-idiotypic antibody. In another embodiment, the protein in the conjugate molecule is a peptide ligand and the capture reagent is an antibody or antigen-binding fragment that specifically binds to the peptide ligand. In other embodiments, the capture reagent can be a protein or fragment thereof that specifically binds to the protein component of the conjugate molecule. In these embodiments, the protein in the conjugate molecule can be an antibody and the capture reagent can be a target antigen of the antibody, protein A, or protein G. In other such embodiments, the protein in the conjugate molecule is a ligand of a cell-surface receptor and the capture reagent is the receptor or a ligand-binding fragment thereof.

The detection reagent employed in the methods of the invention comprises a detectable label coupled to a binding partner, wherein the binding partner specifically binds to either the protein in the conjugate molecule or the tag covalently linked to the TFO. The detectable label coupled to the binding partner can be any type of signal-generating entity, such as a fluorophore, metallic nanoparticle, metallic nanoshell, enzyme, or electrochemiluminescence (ECL) luminophore. In some embodiments of the methods of the invention, the binding partner specifically binds to the protein in the conjugate molecule. In these embodiments, the binding partner can be an antibody or antigen-binding fragment that specifically binds to the protein in the conjugate molecule. In one such embodiment, the protein in the conjugate molecule is an antibody and the binding partner is an anti-Fc region antibody or an anti-idiotypic antibody. In another embodiment, the protein in the conjugate molecule is a peptide ligand and the binding partner is an antibody or antigen-binding fragment that specifically binds to the peptide ligand. In other embodiments, the binding partner can be a protein or fragment thereof that specifically binds to the protein component of the conjugate molecule. For instance, in one embodiment, the protein in the conjugate molecule is an antibody or antigen-binding fragment and the binding partner is a target antigen of the antibody or antigen-binding fragment. In another embodiment, the protein in the conjugate molecule is a ligand of a cell-surface receptor and the binding partner is the receptor or a ligand-binding fragment thereof.

In other embodiments of the methods of the invention, the binding partner in the detection reagent specifically binds to the tag covalently linked to the TFO. In such embodiments, the binding partner can be an antibody or antigen-binding fragment that specifically binds to the tag. For instance, in one embodiment, the tag is digoxigenin and the binding partner is an antibody or antigen-binding fragment that specifically binds to digoxigenin. In other embodiments, the binding partner is a protein or peptide that specifically binds to the tag. In these embodiments, the tag can be biotin and the binding partner can be streptavidin.

The methods of the invention can be used to detect or measure various types of protein-polynucleotide conjugate molecules. The polynucleotide component of the conjugate molecules can be an siRNA, an shRNA, a miRNA, a pre-miRNA, a miRNA mimetic, an anti-miRNA oligonucleotide, or an antisense oligonucleotide. The protein component of the conjugate molecule can be an antibody, antigen-binding fragment (e.g. a scFv, a Fab fragment, a Fab' fragment, a F(ab')$_2$ fragment, or an Fv fragment), or a ligand. In some embodiments, the antibody, antigen-binding fragment, or ligand specifically bind to a receptor expressed by a particular cell type or tissue. In some embodiments, the protein-polynucleotide conjugate molecule to be detected or measured with the methods of the invention is an antibody-siRNA conjugate molecule. In other embodiments, the protein-polynucleotide conjugate molecule to be detected or measured with the methods of the invention is a ligand-siRNA conjugate molecule.

The methods of the invention can be used to detect or measure protein-polynucleotide conjugate molecules in a variety of sample types. In some embodiments, the sample is a biological sample, such as serum, plasma, cell lysate, or tissue (e.g. tissue homogenate). Such samples may be obtained from animal or human subjects who have been administered the protein-polynucleotide conjugate molecules. In some embodiments, the samples are obtained from cell cultures (e.g. supernatants or lysates) that have been exposed to the protein-polynucleotide conjugate molecules. In other embodiments, the sample is obtained from a step in the manufacturing process for the conjugate molecule, such as a reaction mixture or product from a step in the synthetic process for the conjugate molecule. In still other embodiments, the methods of the invention are used as part of a quality control or lot release process and the sample is drug substance or drug product.

DETAILED DESCRIPTION

Figure 1:
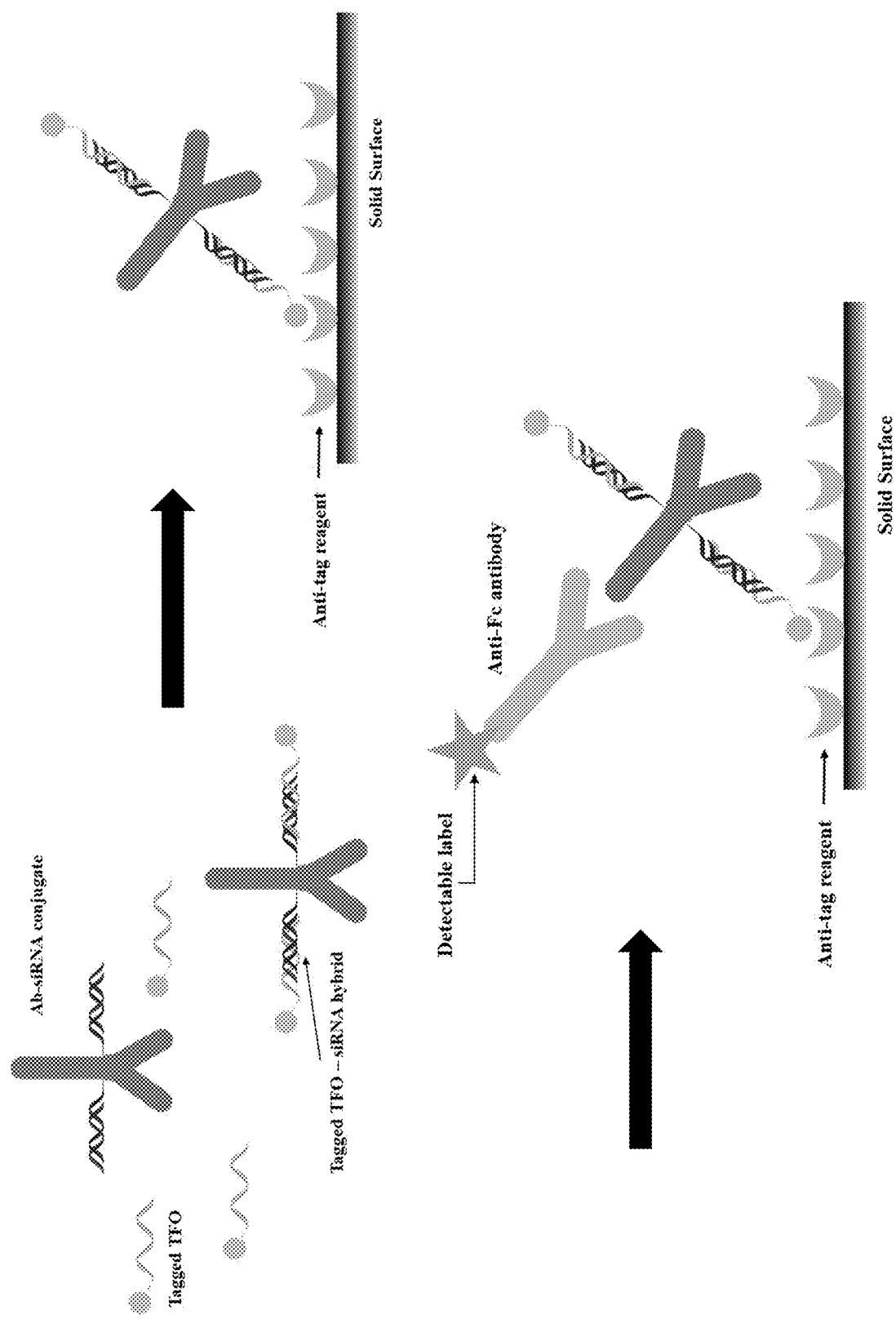
FIG. 1 is a schematic illustrating one format of the assay method of the invention. In this embodiment, a tagged triplex forming oligonucleotide (TFO), e.g. biotinylated TFO, is contacted with a sample containing antibody-siRNA conjugate molecules under hybridization conditions that allow the tagged TFO to form a triplex with the siRNA component of the antibody-siRNA conjugate. The hybridization mixture is contacted with a surface coated with a capture reagent that specifically binds to the tag covalently attached to the TFO (e.g. streptavidin). The antibody-siRNA conjugate molecules that comprise a tagged TFO-siRNA hybrid are thereby immobilized to the surface via the capture reagent—tag interaction (e.g. biotin-streptavidin interaction). Detection and quantification of the immobilized conjugate is subsequently accomplished using a labeled binding partner that specifically binds to the antibody, such as a ruthenium-labeled anti-Fc antibody.

The present invention relates to the development of methods to detect and quantify intact protein-polynucleotide conjugate molecules in various sample matrices, including complex biological samples, such as serum and tissue homogenates. The methods utilize tagged triplex forming oligonucleotides in combination with protein-specific binding partners in sandwich-based formats to determine the presence of the polynucleotide and protein components of the conjugate in the same molecule (i.e. that the conjugate is intact). The methods of the invention are useful in a variety of applications, including the synthesis, stability, and screening of protein-polynucleotide conjugate molecules. The methods can also be employed in pharmacokinetic and drug metabolism studies to understand the clearance profile of intact protein-polynucleotide conjugate molecules and their metabolic degradation in vivo. The methods also find use in quality control and lot release of drug substance and drug product formulations comprising therapeutic protein-polynucleotide conjugate molecules.

The methods of the invention entail contacting a sample comprising a protein-polynucleotide conjugate with a triplex forming oligonucleotide (TFO). A TFO is an oligonucleotide that binds in the major groove of a double-stranded RNA or DNA molecule via Hoogsteen or reverse Hoogsteen hydrogen bonds in a sequence-specific manner. Pyrimidine-rich strands bind by Hoogsteen base-pairing in a parallel orientation with the purine-rich strand in the duplex, with thymine (T) and cytosine (C) in the TFO recognizing adenine (A)-T and guanine (G)-C base pairs to generate T-AT and C$^+$-GC base triplets, respectively. Purine-rich strands bind by reverse Hoogsteen base-pairing in an anti-parallel orientation with the purine-rich strand in the duplex, with A and G in the TFO recognizing AT and GC base pairs to generate A-AT and G-GC base triplets, respectively. TFOs containing base modifications or nucleoside analogs can form triplexes with duplex strands containing a mixture of purine and pyrimidine nucleotides (see, e.g., Rusling et al., Nucleic Acids Res., Vol. 33:3025-3032, 2005).

TFOs used in the methods of the invention generally are at least about 15 nucleotides in length. In some embodiments, the TFO is about 15 to about 30 nucleotides in length. In certain embodiments, the TFO may have the same length as the polynucleotide in the protein-polynucleotide conjugate. For instance, the TFO may have the same length as a single-stranded polynucleotide (e.g. antisense oligonucleotide) in the protein-polynucleotide conjugate. In another embodiment, the TFO may have the same length as one of the strands in a double-stranded polynucleotide (e.g. siRNA) in the protein-polynucleotide conjugate. In these and other embodiments, the TFO may be about 17, 18, 19, 20, 21, 22, 23, 24, 25, or 26 nucleotides in length. In one embodiment, the TFO is about 19 nucleotides in length. In another embodiment, the TFO is about 21 nucleotides in length.

In certain embodiments, the TFO has a sequence that is complementary to the sequence of the polynucleotide in the conjugate molecule. A first sequence is "complementary" to a second sequence if a polynucleotide comprising the first sequence can hybridize to a polynucleotide comprising the second sequence to form a duplex or triplex region under certain conditions. "Hybridize" or "hybridization" refers to the pairing of complementary polynucleotides, typically via hydrogen bonding (e.g. Watson-Crick, Hoogsteen or reverse Hoogsteen hydrogen bonding) between complementary bases in the two polynucleotides. A first sequence is considered to be fully complementary (100% complementary) to a second sequence if a polynucleotide comprising the first sequence base pairs with a polynucleotide comprising the second sequence over the entire length of one or both nucleotide sequences without any mismatches.

In some embodiments, the TFO has a sequence that is fully complementary to the sequence of the polynucleotide in the conjugate molecule, e.g. the sequence of the TFO is complementary to the sequence of the polynucleotide over the entire length of the TFO. In embodiments in which the polynucleotide in the conjugate molecule is a double-stranded polynucleotide, the TFO may be complementary (e.g. fully complementary) to one of the strands of the double-stranded polynucleotide. For instance, in certain such embodiments, the TFO is complementary (e.g. fully complementary) to the strand of the double-stranded polynucleotide that is covalently linked to the protein molecule. In embodiments in which the polynucleotide in the conjugate molecule is an siRNA that comprises a sense strand and an antisense strand, the TFO has a sequence that is complementary (e.g. fully complementary) to the sequence of the sense strand. In other embodiments in which the polynucleotide in the conjugate molecule is an siRNA, the TFO has a sequence that is complementary (e.g. fully complementary) to the sequence of the antisense strand. The strand of an siRNA comprising a region having a sequence that is complementary to a target sequence (e.g. target mRNA) is referred to as the "antisense strand." The "sense strand" refers to the strand that includes a region that is complementary to a region of the antisense strand. In some embodiments, the sense strand may comprise a region that has a sequence that is identical to the target sequence.

In certain embodiments, the TFO used in the methods of the invention comprises one or more modified nucleotides.

A "modified nucleotide" refers to a nucleotide that has one or more chemical modifications to the nucleoside, nucleobase, pentose ring, or phosphate group. As used herein, modified nucleotides do not encompass ribonucleotides containing adenosine monophosphate, guanosine monophosphate, uridine monophosphate, and cytidine monophosphate, or deoxyribonucleotides containing deoxyadenosine monophosphate, deoxyguanosine monophosphate, deoxythymidine monophosphate, and deoxycytidine monophosphate. However, the TFO may comprise combinations of modified nucleotides, ribonucleotides, and deoxyribonucleotides. Modified nucleotides that have been reported to promote triplex formation include 2'-aminoethoxy-5-(3-aminoprop-1-ynyl)uridine (BAU), 3-methyl-2 aminopyridine ($^{Me}$P), 6-(3-aminopropyl)-7-methyl-3H-pyrrolo[2,3-d]pyrimidin-2(7H)-one ($^{A}$PP), N-(4-(3-acetamidophenyl)thiazol-2-yl-acetamide), locked nucleic acid (LNA; 2'-O, 4'-C-methylene-β-D-ribofuranosyl nucleotide), ethylene-bridged nucleic acid (ENA; 2'-O, 4'-C-ethylene-β-D-ribofuranosyl nucleotide), 2'-O,4'-C-aminomethylene bridged nucleic acid (2',4'-BNA$^{NC}$), 5-methyl cytosine, 2-thio uridine, 5-propynyl-deoxyuridine, 8-aminopurines, 2'-deoxy-6-thioguanosines, universal bases, 2'-aminoethylribonucleotides, 2'-O-alky nucleotides (e.g., 2'-O-methyl nucleotides), and nucleotides with modified internucleoside linkages (e.g. phosphoramidate internucleoside linkages, phosphorothioate internucleoside linkages, and peptide nucleic acids (PNA)). See, e.g., Rusling et al., Nucleic Acids Res., Vol. 33:3025-3032, 2005; Duca et al., Nucleic Acids Res., Vol. 36: 5123-5138, 2008; and Zhou et al., Nucleic Acids Res., Vol. 41: 6664-6673, 2013. The TFO employed in the methods of the invention may comprise one or more of these modified nucleotides or combinations thereof.

In some embodiments, the TFO comprises one or more nucleotides with a bicyclic sugar modification. A "bicyclic sugar modification" refers to a modification of the pentose ring where a bridge connects two atoms of the ring to form a second ring resulting in a bicyclic sugar structure. In some embodiments, the bicyclic sugar modification comprises a bridge between the 4' and 2' carbons of the pentose ring. Nucleotides comprising a sugar moiety with a bicyclic sugar modification are referred to herein as bicyclic nucleic acids or BNAs. Exemplary bicyclic sugar modifications include, but are not limited to, α-L-Methyleneoxy (4'-CH$_2$—O-2') bicyclic nucleic acid (BNA); β-D-Methyleneoxy (4'-CH$_2$—O-2') BNA (also referred to as a locked nucleic acid or LNA); Ethyleneoxy (4'-(CH$_2$)$_2$—O-2') BNA (also referred to as ethylene-bridged nucleic acid or ENA); Aminooxy (4'-CH$_2$—O—N(R)-2') BNA; Oxyamino (4'-CH$_2$—N(R)—O-2') BNA; Methyl(methyleneoxy) (4'-CH(CH$_3$)—O-2') BNA (also referred to as constrained ethyl or cEt); methylene-thio (4'-CH$_2$—S-2') BNA; methylene-amino (4'-CH$_2$—N(R)-2') BNA; methyl carbocyclic (4'-CH$_2$—CH(CH$_3$)-2') BNA; propylene carbocyclic (4'-(CH$_2$)3-2') BNA; and Methoxy(ethyleneoxy) (4'-CH(CH$_2$OMe)-O-2') BNA (also referred to as constrained MOE or cMOE). In one embodiment, the TFO comprises one or more LNA monomers. In another embodiment, the TFO comprises one or more ENA monomers.

In certain embodiments, the TFO used in the methods of the invention comprises a mixture of LNA monomers and deoxyribonucleotides. Generally, the number and placement of the LNA monomers in the TFO is such that the melting temperature (Tm) of a complex between the TFO and a complementary RNA strand is about 75° C. to about 85° C., about 77° C. to about 82° C., or about 80° C. The Tm can be measured experimentally or can be predicted using various thermodynamic models, such as the nearest-neighbor model (see, e.g., Owczarzy et al., Biopolymers, Vol. 44 (3): 217-239, 1997; SantaLucia, Proc. Natl. Acad. Sci. USA, Vol. 95(4): 1460-1465, 1998). Prediction tools for predicting the Tm of LNA monomer-containing oligonucleotides are also publicly available, such as the RNA Tm prediction algorithm from Exiqon (see prediction tool available at exiqon.com/ls/Pages/ExiqonTMPredictionTool).

In some embodiments, about 30% to about 40% of the nucleotides in the TFO are LNA monomers. For instance, by way of illustration, a TFO having a length of 21 nucleotides may have 6 to 8 LNA monomers. In certain embodiments, the TFO having a length of about 15 nucleotides to about 30 nucleotides may have 4 to 12 LNA monomers, 5 to 10 LNA monomers, or 6 to 8 LNA monomers. The non-LNA monomers can be modified nucleotides (e.g. any of the modified nucleotides described herein), ribonucleotides, or deoxyribonucleotides. In particular embodiments, the non-LNA monomers are deoxyribonucleotides. In some embodiments, the LNA monomers are placed as uniformly as possible throughout the TFO while maintaining the target Tm range (about 75° C. to about 85° C.). In related embodiments, the TFO does not have more than four consecutive LNA monomers.

The TFOs can readily be made using techniques known in the art, for example, using conventional nucleic acid solid phase synthesis. The TFOs can be assembled on a suitable nucleic acid synthesizer utilizing standard nucleotide or nucleoside precursors (e.g. phosphoramidites). Automated nucleic acid synthesizers are sold commercially by several vendors, including DNA/RNA synthesizers from Applied Biosystems (Foster City, CA), MerMade synthesizers from BioAutomation (Irving, TX), and OligoPilot synthesizers from GE Healthcare Life Sciences (Pittsburgh, PA). TFOs with desired sequences and chemical modifications can also be purchased commercially as custom oligonucleotide synthesis is available from several vendors, such as Exiqon/Qiagen (Venlo, Netherlands), Sigma-Aldrich (St. Louis, MO), and Dharmacon (Lafayette, CO).

Preferably, the TFOs employed in the methods of the invention are covalently linked to a tag. The tag can be any molecular entity capable of being covalently attached to the TFO and to which a specific binding partner is available or can be generated. For instance, in some embodiments, the tag is a protein, peptide, glycopeptide, carbohydrate, or hapten. In some embodiments, the tag is sufficiently immunogenic in an animal species such that tag-specific antibodies can be raised against the tag. In certain embodiments, the tag is a hapten. The hapten can be, but is not limited to, biotin, digoxigenin, or 2,4-dinitrophenol. In one embodiment, the tag is biotin. In another embodiment, the tag is digoxigenin.

The tag can be covalently attached at the 5' or 3' end of the TFO or it can be attached to a nucleotide incorporated into the TFO (e.g. via modification of the sugar or backbone component of the nucleotide). In one embodiment, the tag is covalently attached to the 3' end of the TFO. In another embodiment, the tag is covalently attached to the 5' end of the TFO. The tag can be attached to the TFO using methods known in the art, such as succinimide ester coupling, thiol coupling, click chemistry, and those methods described in Zearfoss and Ryder, Methods Mol. Biol., Vol. 941:181-193, 2012. TFOs covalently attached to desired tags can also be prepared by commercial vendors offering custom oligonucleotide synthesis services, such as the vendors described above.

In some embodiments, the methods of the invention comprise forming a hybridization mixture by contacting a sample comprising a target protein-polynucleotide conjugate molecule with a tagged TFO under conditions that allow the TFO to hybridize to the polynucleotide in the conjugate molecule. The hybridization conditions can be adjusted based on the type of target polynucleotide (e.g. single-stranded or double-stranded), and the sequence and degree of chemical modification of the TFO. However, generally, hybridization of the TFO to the polynucleotide component of the conjugate molecule that may be present in the sample is conducted at a temperature of about 25° C. to about 60° C., about 45° C. to about 55° C., about 50° C. to about 55° C., or about 52° C. for about 30 min to about 90 min, or about 60 min. In certain embodiments, hybridization of the TFO to the polynucleotide component of the conjugate molecule is not conducted at a temperature above 65° C. A suitable hybridization buffer may include a buffer that maintains the pH in a range of 7 to 8, a salt, and a surfactant. An exemplary hybridization buffer comprises 30 mM sodium phosphate buffer, pH 7.0, 500 mM NaCl, 5 mM EDTA, and 0.2% (v/v) Tween 20. Additional suitable hybridization buffers are known to those of skill in the art.

Conjugate molecules comprising tagged TFOs hybridized to the polynucleotide component can be isolated from the sample using a capture reagent that specifically binds to the tag covalently linked to the TFO. For instance, in some embodiments, the methods of the invention comprise contacting a sample with a TFO that is covalently linked to a tag under conditions that allow the TFO to hybridize to the polynucleotide in the conjugate molecule, thereby forming a hybridization mixture, and contacting the hybridization mixture with a surface comprising a capture reagent that specifically binds to the tag covalently linked to the TFO. In such embodiments, the capture reagent can be any molecule that is able to specifically bind or recognize the tag. A molecule "specifically binds" to a target molecule when it has a significantly higher binding affinity for, and consequently is capable of distinguishing, that target molecule compared to its affinity for other unrelated molecules, under similar binding assay conditions. In some embodiments, the capture reagent may bind to the tag with an equilibrium dissociation constant ($K_D$) of $\leq 1\times10^{-6}$ M. In other embodiments, the capture reagent may bind to the tag with an equilibrium dissociation constant $K_D$ of $\leq 1\times10^{-8}$ M.

Capture reagents that specifically bind to the tag include, but are not limited to, polypeptides, aptamers, glycopeptides, lectins, and antibodies or antigen-binding fragments thereof. In some embodiments, the capture reagent that specifically binds to the tag is an antibody or an antigen-binding fragment thereof. An antigen-binding fragment of an antibody is a portion of an antibody that lacks at least some of the amino acids present in a full-length heavy chain and/or light chain, but which is still capable of specifically binding to an antigen. An antigen-binding fragment includes, but is not limited to, a single-chain variable fragment (scFv), a nanobody (e.g. VH domain of camelid heavy chain antibodies), VHH fragment, a Fab fragment, a Fab' fragment, a F(ab)'$_2$ fragment, an Fv fragment, an Fd fragment, and a complementarity determining region (CDR) fragment. In certain embodiments, the capture reagent is a monoclonal antibody or antigen-binding fragment thereof that specifically binds to the tag.

In some embodiments of the methods of the invention, the tag covalently linked to the TFO is biotin and the capture reagent is avidin, streptavidin, neutravidin, or an anti-biotin antibody or antigen-binding fragment thereof. In one embodiment, the tag is biotin and the capture reagent is streptavidin. In other embodiments of the methods of the invention, the tag covalently linked to the TFO is digoxigenin and the capture reagent is an anti-digoxigenin antibody or antigen-binding fragment thereof.

Alternatively, conjugate molecules comprising tagged TFOs hybridized to the polynucleotide component can be isolated from the sample using a capture reagent that specifically binds to the protein component of the conjugate molecules. For example, in some embodiments, the methods of the invention comprise contacting a sample with a TFO that is covalently linked to a tag under conditions that allow the TFO to hybridize to the polynucleotide in the conjugate molecule, thereby forming a hybridization mixture, and contacting the hybridization mixture with a surface comprising a capture reagent that specifically binds to the protein in the conjugate molecule. In such embodiments, the capture reagent can be any molecule that is able to specifically bind to the protein or a marker entity incorporated into the protein. In some embodiments, the capture reagent may bind to the protein or marker entity with an equilibrium dissociation constant $K_D$ of $\leq 1\times10^{-6}$ M. In other embodiments, the capture reagent may bind to the protein or marker entity with an equilibrium dissociation constant $K_D$ of $\leq 1\times10^{-8}$ M.

Capture reagents that specifically bind to the protein include, but are not limited to, polypeptides, aptamers, glycopeptides, ligands, receptors, polysaccharides, antigens, and antibodies or antigen-binding fragments thereof. In some embodiments, the capture reagent that specifically binds to the protein in the conjugate molecule is an antibody or an antigen-binding fragment thereof. In certain embodiments, the protein in the conjugate molecule is a ligand (e.g. a ligand of a cell-surface receptor) and the capture reagent is the receptor for the ligand or a fragment of the receptor that contains the ligand-binding domain (e.g. a ligand-binding fragment of the receptor). In other embodiments, the protein in the conjugate molecule is an antibody or antigen-binding fragment thereof and the capture reagent is a target antigen (or fragment of the antigen containing the epitope) of the antibody or antigen-binding fragment. In still other embodiments, the protein in the conjugate molecule is an antibody and the capture reagent is a protein that specifically binds to the Fc region of the antibody, such as an anti-Fc region antibody, protein A, or protein G. In yet other embodiments, the protein in the conjugate molecule is an antibody or antigen-binding fragment thereof and the capture reagent is an anti-idiotypic antibody. An anti-idiotypic antibody is an antibody that binds to the idiotype of another antibody. An idiotype of an antibody is the specific combination of idiotopes present within the antibody's variable regions.

In some embodiments of the methods of the invention, the capture reagent specifically binds to a marker entity incorporated into the protein in the conjugate molecule. Marker entities are peptide sequences that can be fused to the protein in the conjugate molecule, e.g., at the N-terminus or C-terminus. Examples of marker entities include, but are not limited to, polyhistidine (e.g. 6-8 histidine residues), calmodulin binding protein, myc sequence (EQKLISEEDL; SEQ ID NO: 4), hemagglutinin (HA) sequence (YPYDVPDYA; SEQ ID NO: 5), and FLAG sequence (DYKDDDDK; SEQ ID NO: 6). In certain embodiments, the capture reagent is an antibody or antigen-binding fragment that binds to the marker entity fused to the protein in the conjugate molecule (e.g. capture reagent is an anti-myc, anti-HA, or anti-FLAG antibody). In other embodiments, the capture reagent is a protein or other molecule that specifically recognizes or binds the marker entity. For instance, protein molecules fused to calmodulin binding protein can be captured by calmodulin. In still other embodiments, the marker entity is polyhistidine and the capture reagent is nickel, cobalt, or zinc ions.

The capture reagents employed in the methods of the invention are preferably attached to or immobilized on a surface. The surface can be a bead or particle (e.g. a magnetic bead or particle comprising silica, latex, polystyrene, polycarbonate, polyacrylate, or polyvinylidene fluoride (PVDF)), a membrane (e.g. PVDF, nitrocellulose, polyethylene, or nylon membrane), a tube, a resin, a column, an electrode, or a well in an assay plate (e.g. a well in a microtiter plate). Such surfaces can comprise glass, cellulose-based materials, thermoplastic polymers, such as polyethylene, polypropylene, or polyester, sintered structures composed of particulate materials (e.g., glass or various thermoplastic polymers), or cast membrane film composed of nitrocellulose, nylon, polysulfone, or the like. All of these surface materials can be used in suitable shapes, such as films, sheets, or plates, or they may be coated onto or bonded or laminated to appropriate inert carriers, such as paper, glass, plastic films, or fabrics.

The capture reagents can be immobilized on or attached to a surface by a variety of procedures known to those of skill in the art. The capture reagents can be striped, deposited, or printed on the surface followed by drying of the surface to facilitate immobilization. Immobilization of the capture reagents can take place through adsorption or covalent bonding. Depending on the nature of the surface, methods of derivatization to facilitate the formation of covalent bonds between the surface and the capture reagent can be used. Methods of derivatization can include treating the surface with a compound, such as glutaraldehyde or carbodiimide, and applying the capture reagent. The capture reagent can also be attached to the surface indirectly through a moiety coupled to the capture reagent that enables covalent or non-covalent binding, such as a moiety that has a high affinity to a component attached to the surface. For example, the capture reagent can be coupled to biotin, and the component attached to the surface can be avidin, streptavidin, or neutravidin (see, e.g. FIG. 5). Other physical, chemical, or biological methods of immobilizing a macromolecule or other substance either directly or indirectly to a surface are known in the art and can be used to immobilize or attach the capture reagent to a surface.

Once the conjugate molecules comprising tagged TFOs hybridized to the polynucleotide component are bound to the surface through the capture reagents, the methods of the invention comprise contacting the surface with a detection reagent and detecting a signal from a detectable label in the detection reagent. The detection reagent comprises a detectable label coupled to a binding partner, wherein the binding partner specifically binds to either the protein in the conjugate molecule or the tag covalently linked to the TFO. In embodiments of the method in which the conjugate molecules are bound to the surface via a capture reagent that specifically binds to the tag covalently linked to the TFO, the binding partner in the detection reagent specifically binds to the protein in the conjugate molecule. See, e.g., FIG. 1. In such embodiments, the binding partner that specifically binds to the protein in the conjugate molecule can be any molecule that is able to specifically bind to the protein or a marker entity incorporated into the protein. Such binding partners can include, but are not limited to, polypeptides, aptamers, glycopeptides, metal ions, ligands, receptors, polysaccharides, antigens, and antibodies or antigen-binding fragments thereof. In some embodiments, the binding partner in the detection reagent that specifically binds to the protein in the conjugate molecule is an antibody or an antigen-binding fragment thereof. In certain embodiments, the protein in the conjugate molecule is a ligand (e.g. a ligand of a cell-surface receptor) and the binding partner in the detection reagent is the receptor for the ligand or a fragment of the receptor that contains the ligand-binding domain (e.g. a ligand-binding fragment of the receptor). In other embodiments, the protein in the conjugate molecule is an antibody or antigen-binding fragment thereof and the binding partner in the detection reagent is a target antigen (or fragment of the antigen containing the epitope) of the antibody or antigen-binding fragment. In still other embodiments, the protein in the conjugate molecule is an antibody and the binding partner in the detection reagent is a protein that specifically binds to the Fc region of the antibody, such as an anti-Fc region antibody, protein A, or protein G. In yet other embodiments, the protein in the conjugate molecule is an antibody or antigen-binding fragment thereof and the binding partner in the detection reagent is an anti-idiotypic antibody. In some embodiments of the methods of the invention, the binding partner in the detection reagent specifically binds to a marker entity incorporated into the protein in the conjugate molecule, such as any of the marker entities described above. In certain embodiments, the binding partner in the detection reagent is an antibody or antigen-binding fragment that binds to the marker entity fused to the protein in the conjugate molecule (e.g. binding partner is an anti-myc, anti-HA, or anti-FLAG antibody).

In embodiments of the method in which the conjugate molecules are bound to the surface via a capture reagent that specifically binds to the protein in the conjugate molecule, the binding partner in the detection reagent specifically binds to the tag covalently linked to the TFO. See, e.g., FIG. 5. In such embodiments, the binding partner can be any molecule that is able to specifically bind or recognize the tag. Such binding partners can include, but are not limited to, polypeptides, aptamers, glycopeptides, lectins, and antibodies or antigen-binding fragments thereof. In some embodiments, the binding partner in the detection reagent that specifically binds to the tag is an antibody or an antigen-binding fragment thereof. In certain embodiments, the tag covalently linked to the TFO is biotin and the binding partner in the detection reagent is avidin, streptavidin, neutravidin, or an anti-biotin antibody or antigen-binding fragment thereof. In one embodiment, the tag is biotin and the binding partner in the detection reagent is streptavidin. In other embodiments, the tag covalently linked to the TFO is digoxigenin and the binding partner in the detection reagent is an anti-digoxigenin antibody or antigen-binding fragment thereof.

The detectable label in the detection reagent can be any molecular entity that is capable of producing a detectable signal under a particular set of conditions. Conventional labels may be used which are capable, alone or in concert with other compositions or compounds, of providing a detectable signal. The detectable label can be a radiolabel, an enzyme, a fluorophore, a chromophore, a chemiluminescent label, an electrochemiluminescence (ECL) luminophore, a metallic nanoparticle, or a metallic nanoshell.

In one embodiment, the detectable label coupled to the binding partner is a metallic nanoparticle or metallic nanoshell. Suitable metallic nanoparticles or nanoshells for use as the detectable label include, but are not limited to, gold nanoparticles, silver nanoparticles, copper nanoparticles, platinum nanoparticles, cadmium nanoparticles, composite nanoparticles (e.g. silver and gold or copper and silver), gold hollow spheres, gold-coated silica nanoshells, and silica-coated gold shells. In another embodiment, the detectable label coupled to the binding partner is an enzyme that can convert a substrate into a detectable signal, e.g. a colored, fluorescent, or chemiluminescent product. Non-limiting examples of enzymes that are suitable for coupling to the binding partner to produce a detection reagent include alkaline phosphatase, horseradish peroxidase, beta-galactosidase, beta-lactamase, galactose oxidase, lactoperoxidase, luciferase, myeloperoxidase, and amylase. In yet another embodiment, the detectable label coupled to the binding partner is a fluorophore. Exemplary fluorescent molecules suitable for use as detectable labels include fluorescein, Texas-Red, green fluorescent protein, yellow fluorescent protein, cyan fluorescent protein, Alexa dye molecules, rhodamine dye molecules, and the like.

In some embodiments of the methods of the invention, the detectable label coupled to the binding partner is an ECL luminophore. ECL luminophores that can be coupled to the binding partner to produce a detection reagent include, but are not limited to, ruthenium complexes (e.g. tri-2,2'-bipyridylruthenium(II) [$Ru(bpy)_3^{2+}$]), iridium complexes, aluminum complexes, chromium complexes, copper complexes, europium complexes, osmium complexes, platinum complexes, and rhenium complexes, such as those described in Richter, Chem. Rev., Vol. 104: 3003-3036, 2004, Liu et al., Chem. Soc. Rev., Vol. 44, 3117-3142, 2015, and Zhou et al., Dalton Trans., Vol. 46, 355-363, 2017. In certain embodiments, the ECL luminophore coupled to the binding partner in the detection reagent is a ruthenium complex.

Methods of coupling the detectable label to the binding partner are known in the art and can include passive adsorption (e.g. when metallic nanoparticles or nanoshells are the detectable label) and conjugation chemistries, such as succinimide ester coupling to primary amines and maleimide coupling to sulfhydryl groups. Other methods of coupling macromolecules to detectable labels are known to the skilled artisan, who can select the proper method based on the type of desired detectable label to be used and the type of binding partner (e.g. macromolecule) to be labeled.

Following contact of the surface comprising the captured conjugate molecules with the detection reagent, the methods of the invention comprise detecting or measuring a signal from the detectable label in the detection reagent. A signal from the detectable label indicates that the target protein-polynucleotide conjugate molecule is intact, i.e. that the polynucleotide component remains covalently linked to the protein component. The signal to be detected will depend on the type of detection label employed. For instance, signals from metallic nanoparticle or nanoshell labels can be detected by measuring the amount of light scattering or light absorption. Signals from fluorophores or ECL luminophores can be detected or measured as light intensity at particular emission wavelengths. When the detectable label is an enzyme, the signal is produced by adding a substrate of the enzyme that produces a detectable signal, such as a chromogenic, fluorogenic, or chemiluminescent substrate. Instruments, such as spectrophotometers, fluorescent/luminescent plate readers, and other instruments capable of detecting spectral and electrochemical changes are commercially available and known to those of skill in the art. In certain embodiments, detecting a signal from the detectable label provides a qualitative assessment (i.e. intact conjugate molecule is present in the sample). In other embodiments, detecting a signal from the detectable label provides a quantitative measurement of the amount of the intact conjugate molecule in the sample. For example, in certain embodiments, measurements of, e.g., light scattering, light absorption, or fluorescence/luminescence emission allows for the amount of intact conjugate molecule in the sample to be determined quantitatively. Such quantitation can be achieved by measuring the signal from the detectable label in samples containing known amounts of intact conjugate molecules, constructing calibration curves from the data, and determining the amount of intact conjugate molecules in a test sample from the calibration curves.

Any type of protein-polynucleotide conjugate molecule can be detected or measured in a sample using the methods of the invention. The polynucleotide component of the conjugate molecule can be a single-stranded polynucleotide, a double-stranded polynucleotide, or a polynucleotide that comprises both single-stranded and double-stranded regions (e.g. a polynucleotide that contains at least one self-complementary region such that the single polynucleotide folds back on itself to hybridize and generate double-stranded regions). The polynucleotides in the protein-polynucleotide conjugate may be comprised of ribonucleotides, deoxyribonucleotides, modified nucleotides, or combinations thereof. The polynucleotide component of the conjugate molecule can be a small interfering RNA (siRNA), a short hairpin RNA (shRNA), a microRNA (miRNA), a precursor miRNA (pre-miRNA), a miRNA mimetic, an anti-miRNA oligonucleotide (e.g. antagomir and antimiR), or an antisense oligonucleotide. In certain embodiments, the polynucleotide is a therapeutic polynucleotide designed to target a gene or RNA molecule associated with a disease or disorder. In these and other embodiments, the polynucleotide comprises one or more modified nucleotides to enhance the stability or potency of the polynucleotide. Such modified nucleotides can include, but are not limited to, nucleotides with 2' sugar modifications (2'-O-methyl, 2'-methoxyethyl, 2'-fluoro, etc.), abasic nucleotides, inverted nucleotides (3'-3' linked nucleotides), phosphorothioate linked nucleotides, nucleotides with bicyclic sugar modifications (e.g. LNA, ENA), and nucleotides comprising base analogs (e.g. universal bases, 5-methylcytosine, pseudouracil, etc.).

The length of the polynucleotide component of the protein-polynucleotide conjugate will vary depending on the type of polynucleotide (e.g. siRNA, miRNA, antisense oligonucleotide, etc.), but generally will be from about 15 nucleotides in length to about 150 nucleotides in length. For instance, each strand of a double-stranded siRNA molecule, a miRNA molecule, or a miRNA mimetic molecule is typically about 15 nucleotides in length to about 30 nucleotides in length, whereas as a single-stranded shRNA molecule and a pre-miRNA molecule, which fold back on themselves to form stem-loop or hairpin structures, can be from about 35 nucleotides to about 120 nucleotides in length. Antisense oligonucleotides and anti-miRNA oligonucleotides are typically from about 15 nucleotides to about 25 nucleotides in length. In some embodiments, the polynucleotide component in the conjugate molecule to be detected or measured with the methods of the invention is an antisense oligonucleotide. In other embodiments, the polynucleotide component in the conjugate molecule to be detected or measured with the methods of the invention is an siRNA molecule. In such embodiments, the sense strand and antisense strand of the siRNA molecule can independently be about 15 to about 30 nucleotides in length, about 18 to about 26 nucleotides in length, or about 19 to about 21 nucleotides in length.

The protein component of the conjugate molecule can be any protein or fragment thereof to which a polynucleotide can be covalently linked. In some embodiments, the protein component imparts a property or characteristic to the linked polynucleotide, such as a longer circulating serum half-life or targeting to a specific tissue or cell type. In certain embodiments, the protein in the conjugate molecule is an antibody or antigen-binding fragment thereof. In these and other embodiments, the protein in the conjugate molecule targets the conjugate molecule to a specific cell type or tissue, e.g., by specifically binding to a cell-specific or tissue-specific protein. In such embodiments, the polynucleotide component can be a therapeutic polynucleotide. For instance, in one embodiment, the protein is an antibody or antigen-binding fragment thereof that specifically binds to a receptor expressed by the target cell or tissue. By way of example, the protein can be an antibody or antigen-binding fragment that specifically binds to a receptor expressed by hepatocytes, such as the asialoglycoprotein receptor or the LDL receptor, to target the conjugate molecule to the liver. Antibodies that bind to other cell-surface receptors on other target cell types (e.g. B cells, tumor cells, cardiomyocytes, skeletal myocytes, pancreatic cells, neurons, etc.) can be the protein component in the conjugate molecule. In other embodiments, the protein in the conjugate molecule is a ligand. The ligand can be a ligand for a receptor expressed on the surface of a target cell or tissue to which the conjugate molecule is to be delivered. In such embodiments, the protein in the conjugate molecule can be the ligand itself or a peptide fragment or analog of the ligand that retains receptor-binding function.

In certain embodiments, the protein-polynucleotide conjugate molecule to be detected or measured in a sample using the methods of the invention is an antibody-siRNA conjugate molecule. In other embodiments, the protein-polynucleotide conjugate molecule is a peptide ligand-siRNA conjugate molecule. In yet other embodiments, the protein-polynucleotide conjugate molecule is an antibody-antisense oligonucleotide conjugate molecule. In still other embodiments, the protein-polynucleotide conjugate molecule is a peptide ligand-antisense oligonucleotide conjugate molecule. In these embodiments, the siRNA or antisense oligonucleotide components of the conjugate molecules can be therapeutic (i.e. targeted to a gene or RNA molecule associated with a disease or disorder) and the antibody or peptide ligand component of the conjugate molecule can specifically bind to a cell-specific or tissue-specific receptor.

The methods of the invention can be used to detect or measure protein-polynucleotide conjugate molecules in various types of samples. In some embodiments, the sample is a bodily fluid, such as blood, serum, plasma, cerebral spinal fluid, or urine. In other embodiments, the sample is a tissue (e.g. tissue homogenate) or a cell lysate. In these and other embodiments, the sample is obtained from an animal or human subject who has been administered the protein-polynucleotide conjugate molecule. In some embodiments, the samples are obtained from cell cultures that have been exposed to the protein-polynucleotide conjugate molecules. In such embodiments, the sample may be a supernatant of the cell culture or a lysate of the cells in the culture. In one embodiment, the sample is a reaction mixture or product from a step during the synthetic process for the protein-polynucleotide conjugate molecule. In another embodiment, the sample is a lot of drug substance (e.g. an active pharmaceutical ingredient or API). In yet another embodiment, the sample is a lot of drug product (e.g. API formulated with one or more excipients for human use).

The following examples, including the experiments conducted and the results achieved, are provided for illustrative purposes only and are not to be construed as limiting the scope of the appended claims.

EXAMPLES

Example 1. Detection Assay Using Triplex Forming Oligonucleotide as Capture Agent This example describes one format of the assay method of the invention in which a tagged triplex forming oligonucleotide (TFO) is used to capture an antibody-siRNA conjugate in a sample solution and immobilize the conjugate to a solid surface. The conjugate is subsequently detected and quantified using a labeled binding partner that specifically recognizes the antibody. This assay format is schematically shown in FIG. 1.

An antibody-siRNA conjugate was prepared by covalently attaching an siRNA molecule targeting a liver gene to a monoclonal antibody (mAb) directed to the asialoglycoprotein receptor 1 (ASGR1) protein using the method described in Example 10 of WO 2018/039647, which is hereby incorporated by reference. Briefly, an anti-ASGR1 mAb with an E272C mutation in its heavy chain according to the EU numbering scheme (anti-ASGR1 cys mAb) was incubated with a solution of 2.5 mM cystamine and 2.5 mM cysteamine in 40 mM HEPES buffer, pH 7.5-8.5 for 15-20 hrs at RT and subsequently purified to provide a bis-cysteamine-capped anti-ASGR1 cys mAb. The siRNA molecule was comprised of a sense strand and an antisense strand, each of which was 21 nucleotides in length. The siRNA molecule had a 19 base pair duplex region with a 2 nucleotide overhang at the 3' end of the sense and antisense strands. The sense strand of the siRNA duplex had a homoserine-aminohexanoic acid modification at its 3' end, which was further functionalized with a bromoacetyl group using succinimidyl bromoacetate. The bis-cysteamine-capped anti-ASGR1 cys mAb intermediate was partially reduced using tris(2-carboxyethyl)phosphine (TCEP) or triphenylphosphine-3,3',3''-trisulfonic acid trisodium salt (TPPTS). Oxidation of the partially reduced cys mAb was subsequently performed with dehydroascorbic acid (DHAA), and oxidation was carried out at RT until only trace amount of reduced mAb species were observed. The bromoacetyl-siRNA duplex was then added to the reaction mixture, and the alkylation was carried out at RT for 15-48 hrs. The anti-ASGR1 mAb-siRNA conjugates with RNA-to-antibody ratio (RAR) of 1 and 2 were separated using anion exchange chromatography.

The TFO was designed to have a sequence that was fully complementary to the sense strand, which was the strand that was directly linked to the antibody. Locked nucleic acid (LNA) monomers were incorporated into the TFO such that about 30-40% of the nucleotides of the TFO were LNA monomers and the melting temperature (Tm) of a complex between the TFO and a complementary RNA strand was about 80° C. based on the RNA Tm prediction algorithm from Exiqon (see prediction tool available on Exiqon's website at exiqon.com/ls/Pages/ExiqonTMPredictionTool). The LNA monomers were placed as uniformly as possible throughout the TFO while maintaining the target Tm. The TFO was custom synthesized by Exiqon (Vedbaek, Denmark) and labeled with biotin at the 3' end. The sequence of the TFO was: 5'-AAA CTT CAT CTT TCT TCC CAC-3' (SEQ ID NO: 1), where the LNA monomers are indicated by underlining and bold font.

An eleven point standard curve of the anti-ASGR1 antibody-siRNA conjugate (0.04 ng/mL to 2500 ng/mL) was prepared by serially diluting 1 in 3 a 2500 ng/mL stock solution of anti-ASGR1 antibody-siRNA conjugate in sample buffer (10 mM Tris-HCl, 1 mM EDTA, pH 8.0), mouse serum, or mouse liver homogenate. Separately, various concentrations of biotinylated TFO (6.25 nM to 250 nM) were prepared in hybridization buffer (60 mM sodium phosphate dibasic, 1 M NaCl, 5 mM EDTA, 0.2% (v/v) Tween 20, pH 7.0). The biotinylated TFO in hybridization buffer was mixed with each of the samples 1:1 and hybridization proceeded at 52° C. for 1 hour.

Following hybridization, the samples were transferred to a streptavidin-coated microtiter plate and shaken for 30 min. The plate was then washed with wash buffer (imidazole-buffered saline and Tween 20; supplied as a 20×Wash Solution Concentrate from KPL Inc.). Blocking buffer (5% nonfat powdered milk in Tris buffered saline (Blocker™ BLOTTO, ThermoFisher Scientific)) was added to the samples and the plate was shaken for 30 min. The plate was again washed with wash buffer. Subsequently, a ruthenium-labeled mouse monoclonal antibody directed to the Fc region of human immunoglobulin (anti-human Fc antibody; 1 μg/mL) was added to each of the samples in blocking buffer and the plate was shaken for 1 hour. After washing the plate with wash buffer, the signal from the ruthenium label was read using a Meso Scale Diagnostics (MSD) QuickPlex SQ 120 electro-chemiluminescent reader and MSD Read Buffer T with surfactant.

Figure 2A:
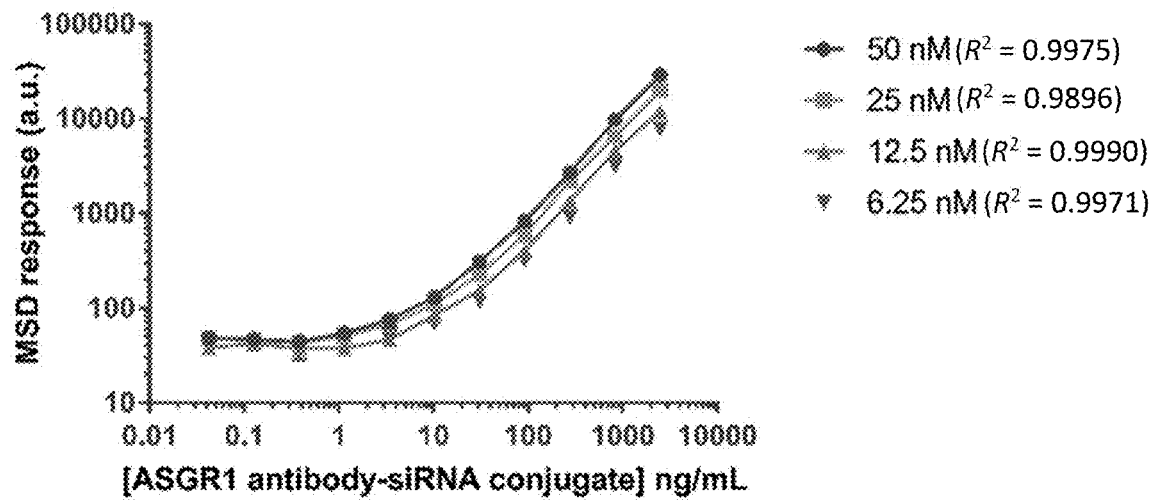
FIGS. 2A and 2B are line graphs of various concentrations of anti-ASGR1 mAb-siRNA conjugate molecules (0.04 ng/mL to 2500 ng/mL) in sample buffer plotted versus electro-chemiluminescent signal in arbitrary units (MSD response) for assays using a low concentration range of biotinylated TFO (FIG. 2A; 6.25 nM to 50 nM) and assays using a high concentration range of biotinylated TFO (FIG. 2B; 50 nM to 250 nM). The assay format depicted in FIG. 1 was employed. Data were fit with a four parameter nonlinear regression model (Marquardt with weighting factor $1/Y^2$). $R^2$ values are shown in parentheses for each of the curves.
Figure 2B:
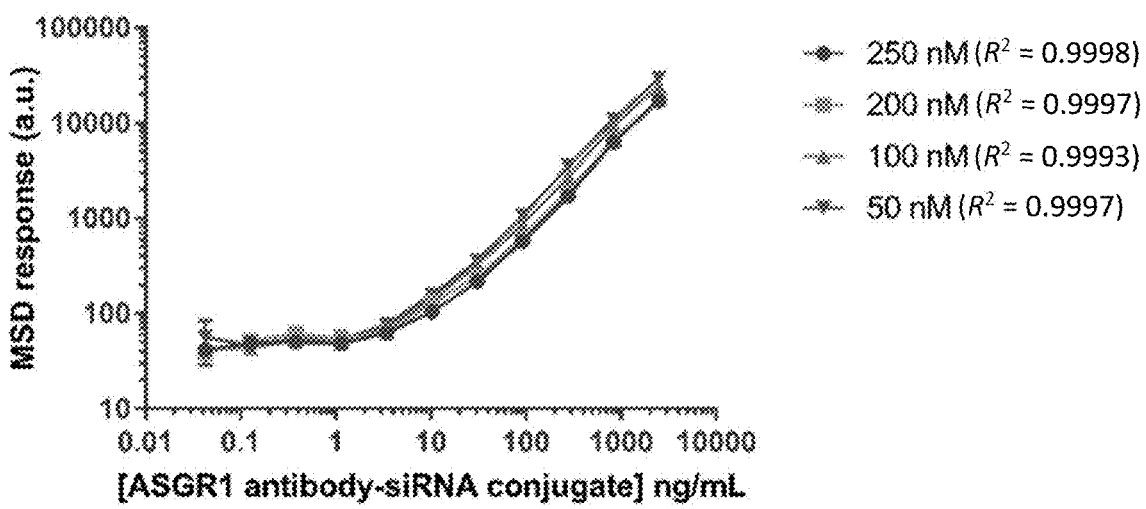
Figure 2C:
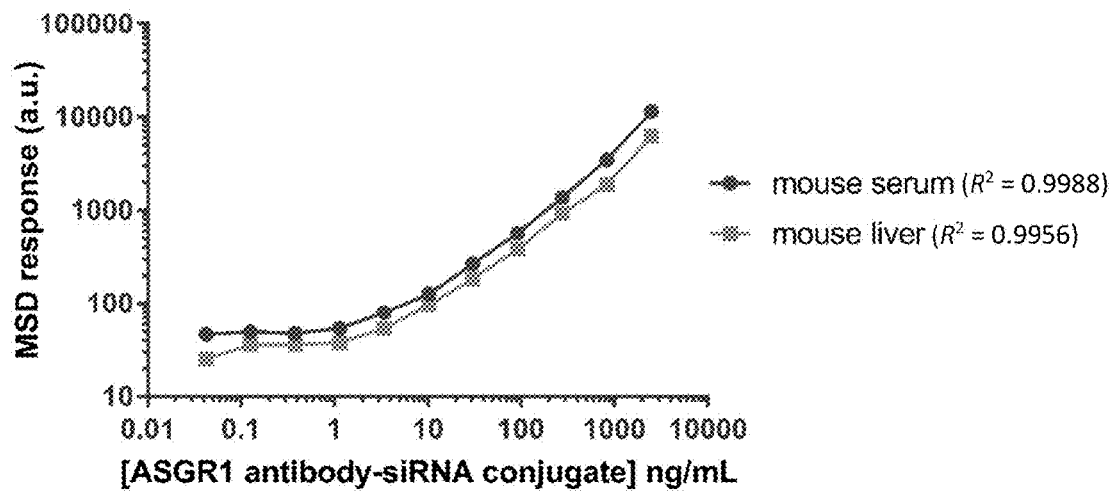
FIG. 2C is a line graph showing the relationship between concentration of anti-ASGR1 mAb-siRNA conjugate molecules (0.04 ng/mL to 2500 ng/mL) in mouse serum or mouse liver homogenate and electro-chemiluminescent signal in arbitrary units (MSD response). The assay format depicted in FIG. 1 was employed. Data were fit with a four parameter nonlinear regression model (Marquardt with weighting factor $1/Y^2$). $R^2$ values are shown in parentheses for each of the two curves. 100 nM of biotinylated TFO was used in the assay to capture the conjugate molecules.

The results of the assay for the detection of anti-ASGR1 mAb-siRNA conjugates in sample buffer at different concentration ranges of biotinylated-TFO are shown in FIGS. 2A and 2B. The data were fit with a four parameter nonlinear regression model (Marquardt with weighting factor 1/Y^2), which yielded $R^2$ values close to 1. The linear range of the assay in buffer was 3.4 ng/mL to 2500 ng/mL. Detection of the anti-ASGR1 mAb-siRNA conjugates could also be achieved in mouse serum and mouse liver homogenate. See FIG. 2C. Using a concentration of biotinylated-TFO of 100 nM, the linear range of the assay in serum and liver homogenate was the same as that for buffer. However, the signal response was reduced in serum and liver homogenate as compared to buffer with the response in serum being about 46% of that in buffer and the response in liver homogenate being about 25% of that in buffer as measured by the difference in slopes of the curves.

To explore the effect of the antibody component of the conjugate on the efficacy of the detection assay, the same siRNA molecule described above (T2 siRNA) was conjugated to a different monoclonal antibody (655 mAb). The 655 mAb was mutated to eliminate its target-binding specificity. Various concentrations (0.04 ng/mL to 2500 ng/mL) of the following conjugate molecules were prepared in sample buffer: (1) 655 mAb-siRNA conjugate molecule with one linked siRNA molecule (T2-655 RAR1), (2) 655 mAb-siRNA conjugate molecule with two linked siRNA molecules (T2-655 RAR2), (3) anti-ASGR1 mAb-siRNA conjugate molecule with one linked siRNA molecule (T2-25B3 RAR1), and (4) anti-ASGR1 mAb-siRNA conjugate molecule with two linked siRNA molecules (T2-25B3 RAR2). The samples were hybridized with 100 nM biotinylated-TFO (SEQ ID NO: 1) in hybridization buffer at 52° C. for 1 hour. Following hybridization, the samples were transferred to streptavidin-coated plates and washed and blocked as described above. Detection of the captured conjugate molecules was achieved using the ruthenium-labeled anti-human Fc mAb and the electro-chemiluminescent signal was read by an MSD QuickPlex SQ 120 electro-chemiluminescent reader.

Figure 3A:
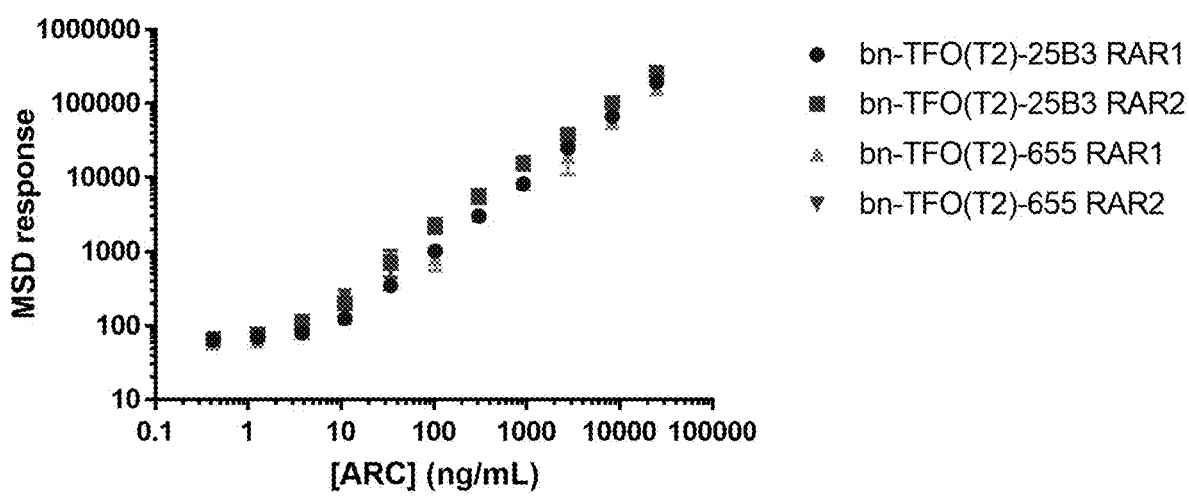
FIG. 3A is a graph showing the relationship between concentration of monoclonal antibody-siRNA conjugate molecules (ARC; 0.04 ng/mL to 2500 ng/mL) in sample buffer and electro-chemiluminescent signal in arbitrary units (MSD response). The assay format depicted in FIG. 1 was employed. siRNA molecule T2 was conjugated to anti-ASGR1 monoclonal antibody 25B3 (T2-25B3) or a non-specific, carrier monoclonal antibody 655 (T2-655). The siRNA molecule was conjugated at an RNA-to-antibody ratio of 1 or 2 (RAR1 or RAR2, respectively). 100 nM of biotinylated TFO was used in the assay to capture the conjugate molecules.
Figure 3B:
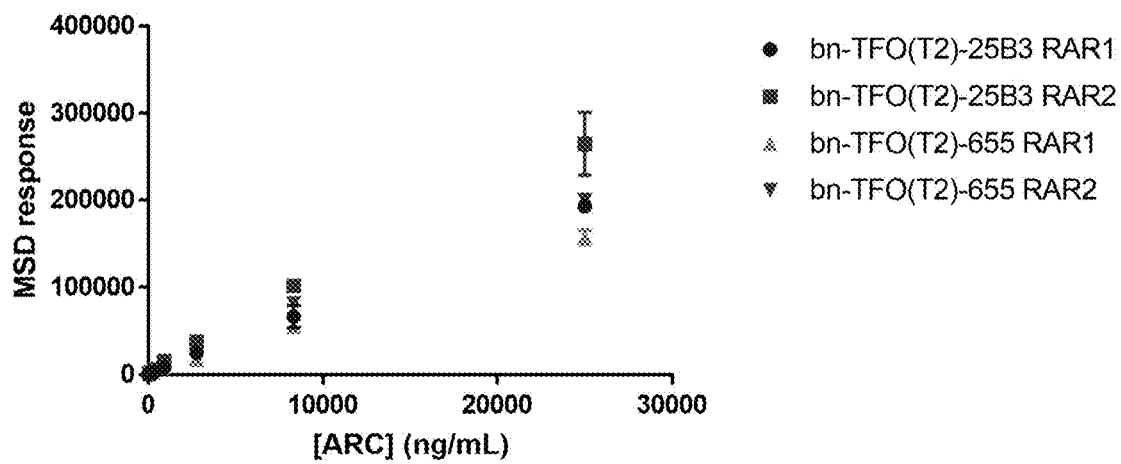
FIG. 3B is a plot of the data shown in FIG. 3A on a linear scale. The data were fit with a linear regression model and the slopes of the fitted lines were calculated. The calculated slopes are shown in the table below the graph. The slopes of the regression lines for the RAR1 conjugates were reduced as compared to the slopes of the regression lines for the RAR2 conjugates. Specifically, the slope for the T2-25B3 RAR1 conjugate was 72% of that for the T2-25B3 RAR2 conjugate, and the slope for the T2-655 RAR1 conjugate was 78% of the that for the T2-655 RAR2 conjugate.

The results of the assay show that the assay performance and sensitivity is similar for the different conjugate molecules despite the difference in the antibody component of the conjugates. See FIG. 3A. The lower limit of quantitation (LLOQ) of <420 pg/mL in this assay run was the same for all four conjugate molecules. To determine whether the assay could distinguish between conjugates having one or two linked siRNA molecules, the data were fitted with a linear regression model and the differences in slopes were compared between RAR1 and RAR2 conjugates. As shown in FIG. 3B, the slopes for the fitted linear regression lines for the RAR1 conjugates were about 75% of those for the RAR2 conjugates (T2-25B3 RAR1 slope 72% of T2-25B3 RAR2 slope; T2-655 RAR1 slope 78% of T2-655 RAR2 slope). Thus, the assay can detect differences between conjugates having one or two linked siRNA molecules under these conditions.

Next, two different antibody-siRNA conjugates, each having a unique siRNA molecule, were evaluated to determine the effect of the siRNA component of the conjugate on the efficacy of the detection assay. The HPRT and C911 siRNA molecules had the same format as the T2 siRNA molecule described above (i.e. 21 mer strands, 19 bp duplex region, 2 nucleotide overhangs at 3' ends), but had different sequences. The HPRT and C911 siRNA molecules were conjugated to an anti-ASGR1 mAb using the method described above. The sequence of the TFO employed in the assay for the HPRT siRNA-antibody conjugate was 5'-ATA AAA TCT ACA GTC ATA GGA-3' (SEQ ID NO: 2), whereas the sequence of the TFO employed in the assay for the C911 siRNA-antibody conjugate was 5'-AAA CTT CAT CAA ACT TCC CAC-3' (SEQ ID NO: 3). LNA monomers are indicated by underlining and bold font. Both TFOs were biotinylated at their 3' ends.

Various concentrations (0.04 ng/mL to 2500 ng/mL) of the following conjugate molecules were prepared in sample buffer: (1) anti-ASGR1 mAb-siRNA conjugate molecule with one linked HPRT siRNA molecule (HPRT-25B3 RAR1), (2) anti-ASGR1 mAb-siRNA conjugate molecule with two linked HPRT siRNA molecules (HPRT-25B3 RAR2), (3) anti-ASGR1 mAb-siRNA conjugate molecule with one linked C911 siRNA molecule (C911-25B3 RAR1), and (4) anti-ASGR1 mAb-siRNA conjugate molecule with two linked C911 siRNA molecules (C911-25B3 RAR2). The samples were hybridized with 100 nM biotinylated-TFO (SEQ ID NO: 2 for HPRT siRNA-mAb conjugate or SEQ ID NO: 3 for C911 siRNA-mAb conjugate) in hybridization buffer at 52° C. for 1 hour. Following hybridization, the samples were transferred to streptavidin-coated plates and washed and blocked as described above. Detection of the captured conjugate molecules was achieved using the ruthenium-labeled anti-human Fc mAb and the electro-chemiluminescent signal was read by an MSD QuickPlex SQ 120 electro-chemiluminescent reader.

Figure 4A:
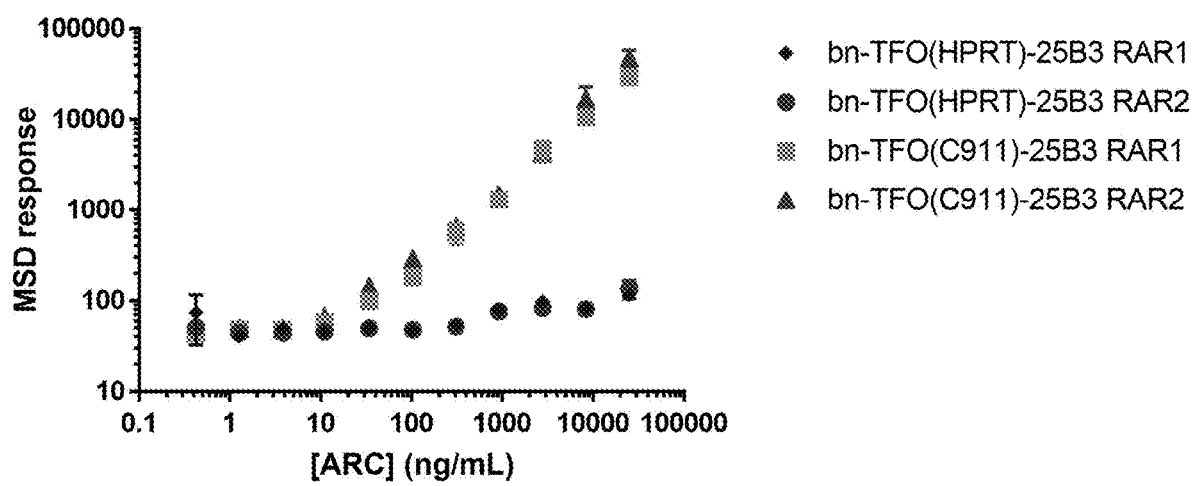
FIG. 4A is a graph showing the relationship between concentration of monoclonal antibody-siRNA conjugate molecules (ARC; 0.04 ng/mL to 2500 ng/mL) in sample buffer and electro-chemiluminescent signal in arbitrary units (MSD response). The assay format depicted in FIG. 1 was employed. siRNA molecule HPRT or siRNA molecule C911 was conjugated to anti-ASGR1 monoclonal antibody 25B3 (HPRT-25B3 or C911-25B3, respectively). The siRNA molecules were conjugated at an RNA-to-antibody ratio of 1 or 2 (RAR1 or RAR2, respectively). 100 nM of biotinylated TFO was used in the assay to capture the conjugate molecules.
Figure 4B:
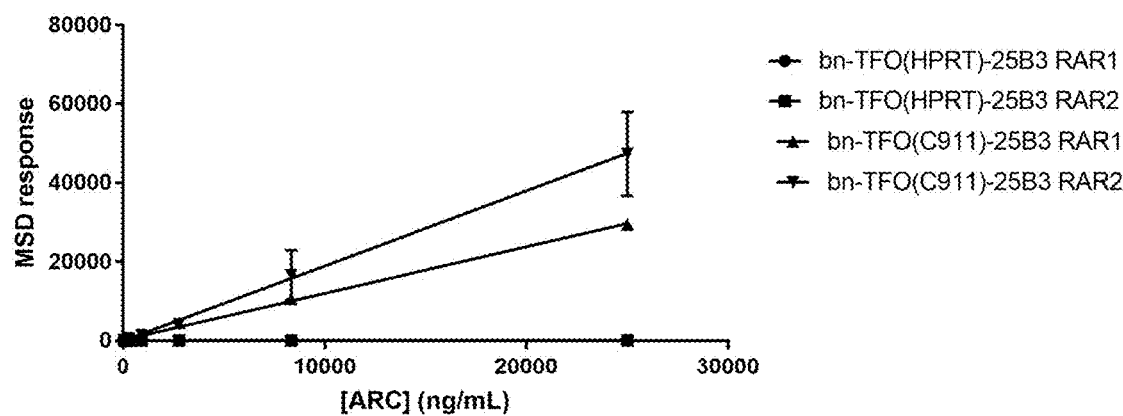
FIG. 4B is a plot of the data shown in FIG. 4A on a linear scale. The data were fit with a linear regression model and the slopes of the fitted lines were calculated. The calculated slopes are shown in the table below the graph. The slopes of the regression lines for the RAR1 conjugates were reduced as compared to the slopes of the regression lines for the RAR2 conjugates. Specifically, the slope for the HPRT-25B3 RAR1 conjugate was 75% of that for the HPRT-25B3 RAR2 conjugate, and the slope for the C911-25B3 RAR1 conjugate was 62% of that for the C911-25B3 RAR2 conjugate.

The results of the assay are shown in FIG. 4A. The sensitivity of the assay appeared to be affected by the specific TFO-siRNA pair as the LLOQ for the C911 siRNA-mAb conjugate molecule was about 100-fold lower than the LLOQ for the HPRT siRNA-mAb conjugate (11 pg/mL for C911-25B3 RAR2 conjugate vs. 926 pg/mL for HPRT-25B3 RAR2 conjugate). However, optimization of the hybridization conditions for each TFO-siRNA pair would likely improve assay sensitivity. Linear regression of the data and comparison of the slopes of the fitted regression lines again demonstrated that the assay can distinguish between conjugates comprising one or two linked siRNA molecules (FIG. 4B). For the HPRT siRNA-mAb conjugates, the RAR1 conjugate had a slope that was 75% of the slope for the RAR2 conjugate. For the C911 siRNA-mAB conjugates, the RAR1 conjugate had a slope that was 62% of the slope for the RAR 2 conjugate.

The results of the series of experiments described in the example demonstrate that one embodiment of the assay methods of the invention in which a tagged TFO is used as a capture agent can selectively detect and quantitate intact antibody-siRNA conjugates in various matrices, including complex matrices, such as serum and tissue homogenate. The assay can also be used to distinguish between antibody-siRNA conjugates that have one or two linked siRNA molecules.

Figure 5:
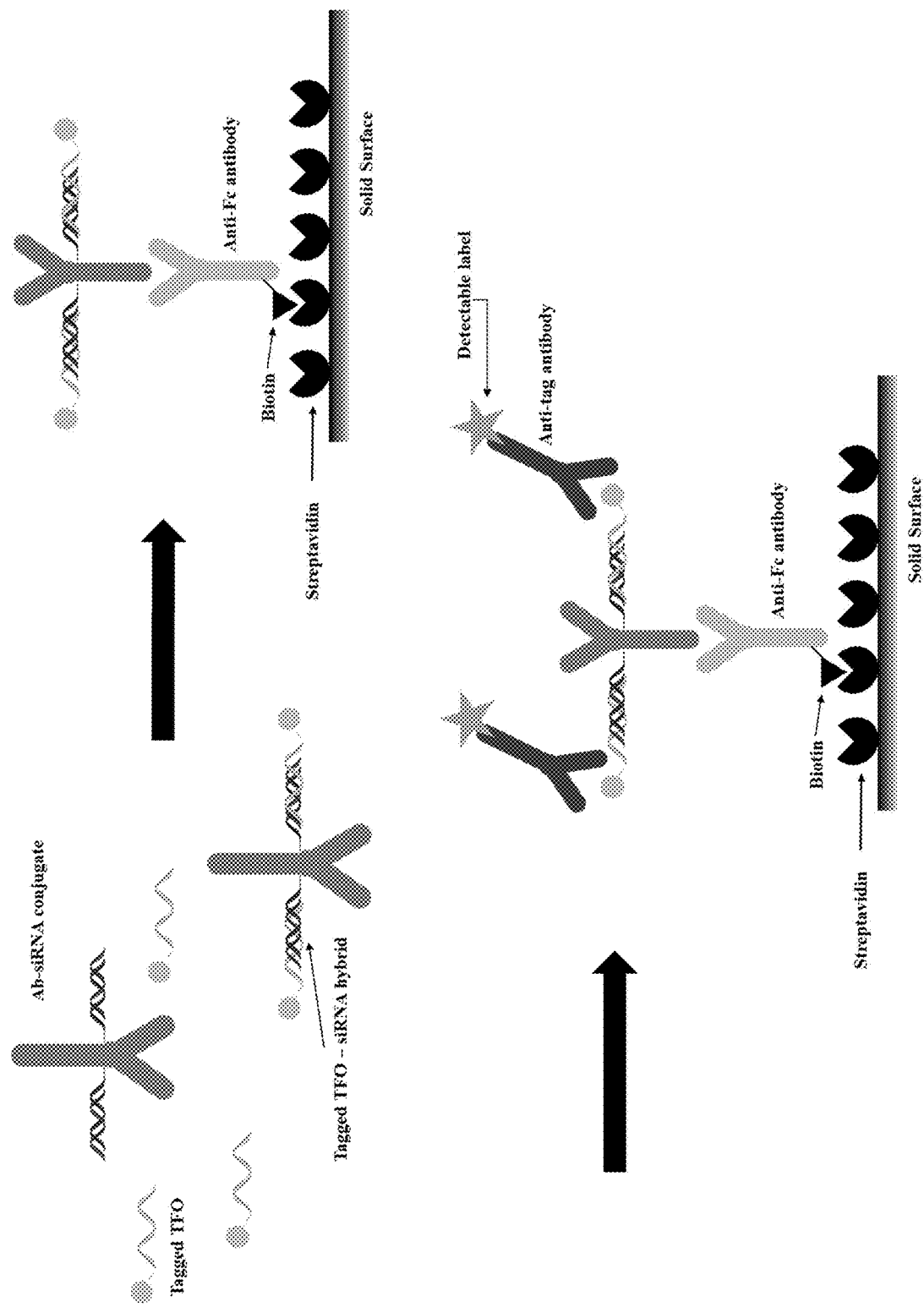
FIG. 5 is a schematic illustrating a second format of the assay method of the invention. In this embodiment, a tagged triplex forming oligonucleotide (TFO), e.g. digoxigenin-labeled TFO, is contacted with a sample containing antibody-siRNA conjugate molecules under hybridization conditions that allow the tagged TFO to form a triplex with the siRNA component of the antibody-siRNA conjugate. The hybridization mixture is contacted with a surface coated with a capture reagent that specifically binds to the antibody component of the antibody-siRNA conjugate (e.g. an anti-Fc antibody or target antigen of the antibody). The capture reagent can be directly coupled to the surface or indirectly coupled through other binding partners, such as biotin and streptavidin as shown in the illustration. Detection and quantification of the immobilized conjugate is subsequently accomplished using a labeled binding partner that specifically binds to the tag covalently attached to the TFO, such as a ruthenium-labeled anti-digoxigenin antibody.

Example 2. Detection Assay Using Triplex Forming Oligonucleotide as Detection Agent This example describes a second format of the assay method of the invention in which a tagged TFO enables detection of an antibody-siRNA conjugate in a sample solution. In this format, the tagged TFO is hybridized to the siRNA component of the antibody-siRNA conjugate and the conjugate is subsequently captured and immobilized to a solid surface via a capture reagent that specifically recognizes the antibody component of the antibody-siRNA conjugate (e.g. the target antigen of the antibody or an anti-Fc antibody). The captured conjugate is detected and quantified using a labeled binding partner that specifically recognizes the tag covalently linked to the TFO. This assay format is schematically shown in FIG. 5.

The 655 mAb-T2 siRNA conjugate and the anti-ASGR1 mAb-T2 siRNA conjugate molecules described in Example 1 were evaluated in this assay format. The sequence of the TFO was: 5'-AA<u>A</u> CT<u>T</u> CA<u>T</u> CT<u>T</u> TC<u>T</u> TCC C<u>A</u>C-3' (SEQ ID NO: 1; LNA monomers are indicated by underlining and bold font), and was labeled at the 3' end with digoxigenin. An eleven point standard curve of each of the antibody-siRNA conjugates (0.38 ng/mL to 25000 ng/mL) was prepared by serially diluting 1 in 3 a 25000 ng/mL stock solution of the antibody-siRNA conjugates in sample buffer (10 mM Tris-HCl, 1 mM EDTA, pH 8.0). The digoxigenin-TFO was prepared in hybridization buffer (60 mM sodium phosphate dibasic, 1 M NaCl, 5 mM EDTA, 0.2% (v/v) Tween 20, pH 7.0) and mixed with each of the samples 1:1. Hybridization proceeded at 52° C. for 1 hour. Separately, a biotin-labeled mouse anti-human Fc antibody in blocking buffer (5% nonfat powdered milk in Tris buffered saline (Blocker™ BLOTTO, ThermoFisher Scientific)) was deposited into the wells of a streptavidin-coated microtiter plate and shaken for 30 min. The plate was then washed with wash buffer (imidazole-buffered saline and Tween 20; supplied as a 20×Wash Solution Concentrate from KPL Inc.) prior to use.

Following hybridization, the samples were transferred to the previously prepared microtiter plate containing bound anti-human Fc antibody and shaken for 1 hour. After washing the plate with wash buffer, a ruthenium-labeled sheep anti-digoxigenin antibody (2 μg/mL) was added to each of the samples in blocking buffer and the plate was shaken for 30 minutes. The plate was again washed with wash buffer and the signal from the ruthenium label was read using a MSD QuickPlex SQ 120 electro-chemiluminescent reader and MSD Read Buffer T with surfactant.

Figure 6:
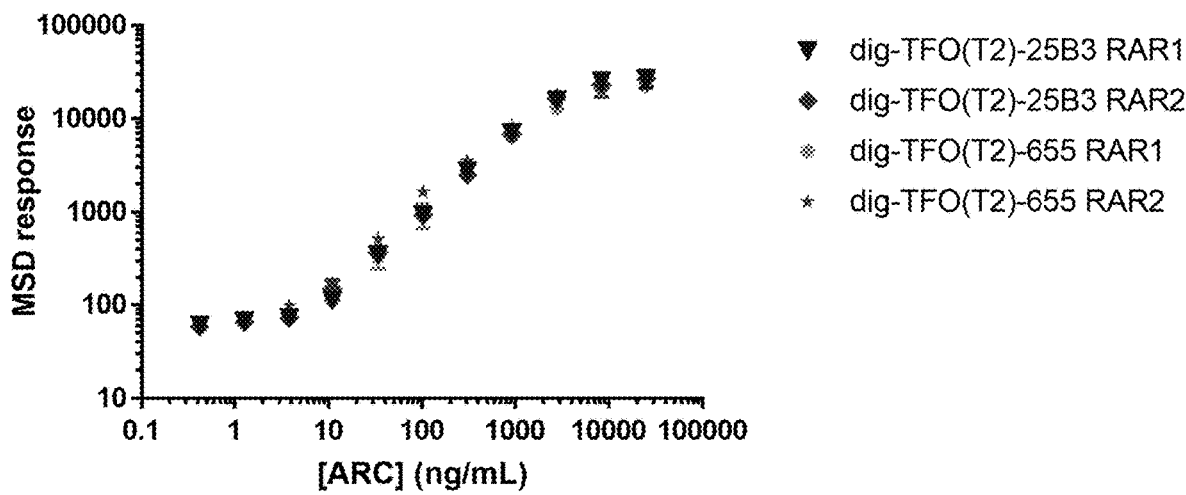
FIG. 6 is a graph showing the relationship between concentration of monoclonal antibody-siRNA conjugate molecules (ARC; 0.38 ng/mL to 25000 ng/mL) in sample buffer and electro-chemiluminescent signal in arbitrary units (MSD response). The assay format depicted in FIG. 5 was employed. siRNA molecule T2 was conjugated to anti-ASGR1 monoclonal antibody 25B3 (T2-25B3) or a non-specific, carrier monoclonal antibody 655 (T2-655). The siRNA molecule was conjugated at an RNA-to-antibody ratio of 1 or 2 (RAR1 or RAR2, respectively). 100 nM of digoxigenin-labeled TFO was used in the assay to hybridize to the siRNA component of the conjugate molecules and enable detection via a ruthenium-labeled anti-digoxigenin antibody.
Figure 7:
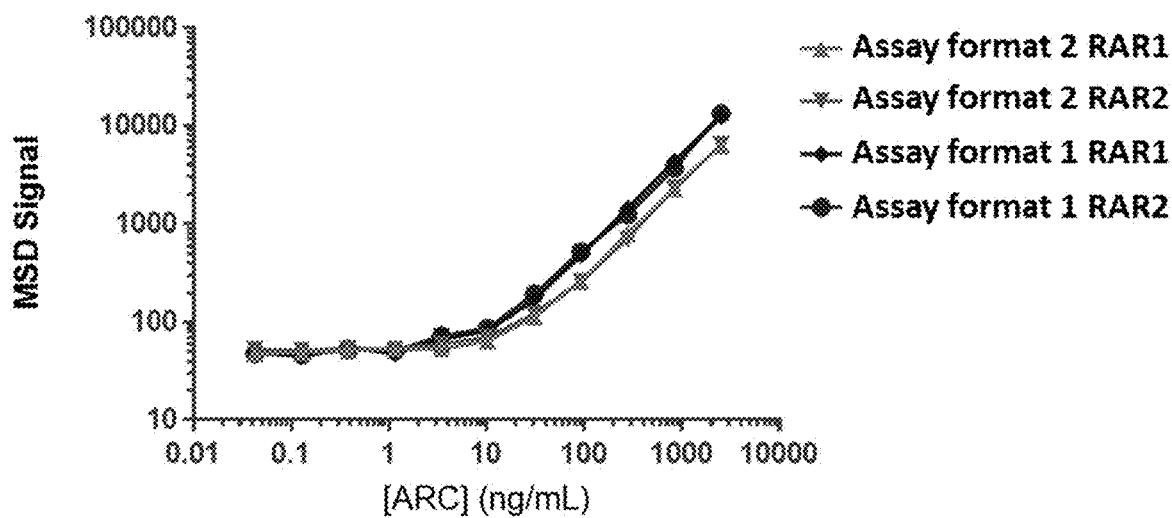
FIG. 7 is a graph showing the relationship between concentration of monoclonal antibody-siRNA conjugate molecules (ARC; 0.04 ng/mL to 2500 ng/mL) in sample buffer and electro-chemiluminescent signal in arbitrary units (MSD signal). siRNA molecule T2 was conjugated to anti-ASGR1 monoclonal antibody 25B3 at an RNA-to-antibody ratio of 1 or 2 (RAR1 or RAR2, respectively). The conjugate molecules were evaluated in two different assay formats: assay format 1 in which the tagged TFO is used for capture (see format depicted in FIG. 1) and assay format 2 in which the tagged TFO is used for detection (see format depicted in FIG. 5). In assay format 1, biotinylated TFO was used in the assay to capture the conjugate molecules and a ruthenium-labeled anti-human Fc antibody was used for detection. In assay format 2, a biotinylated anti-human Fc antibody was used to capture the conjugate molecules and a digoxigenin-labeled TFO in combination with a ruthenium-labeled anti-digoxigenin antibody was used for detection.

The results of the assay are shown in FIG. 6. The LLOQ for all four conjugate molecules was <420 pg/mL, which is similar to the LLOQ for these molecules in the assay format described in Example 1. The antibody component of the conjugate also does not appear to influence the sensitivity of the assay in this format as the LLOQ for both types of conjugates was the same. To compare the performance of this assay format (tagged TFO employed for detection) to the format described in Example 1 (tagged TFO employed for capture), a range of concentrations of the anti-ASGR1 mAb-T2 siRNA conjugate molecule at a RAR1 or RAR2 were tested in both assay formats. As shown in FIG. 7, the dynamic range of the assay for the first format (tagged TFO employed for capture) is greater than that for the second format (tagged TFO employed for detection). The LLOQ for both assay formats was similar.

In another series of experiments, the ability to use the antigen of the antibody component of the conjugates as the capture reagent was explored. First, the antigen binding capability of the antibody-siRNA conjugate was tested to verify that conjugation of the siRNA molecule did not impact the antibody-antigen interaction. The binding affinity and kinetics of the anti-ASGR1 mAb-T2 siRNA RAR2 conjugate molecule for human ASGR1 was determined by bio-layer interferometry using a streptavidin biosensor loaded with a biotinylated fragment of the human ASGR1 protein containing the extracellular domain on an Octet® HTX instrument (Pall ForteBio). The conjugate molecule exhibited similar binding affinity and kinetics to human ASGR1 as compared to the unconjugated anti-ASGR1 antibody (data not shown), indicating that siRNA conjugation did not affect binding of the antibody to its target. The presence of the TFO also did not impact antigen binding because the streptavidin sensor loaded with an anti-ASGR1 mAb-siRNA conjugate containing a hybridized biotinylated TFO was able to bind to the carbohydrate binding domain of human ASGR1 (data not shown).

Next, the detection assay described above was repeated, except that biotinylated human ASGR1 was used as the capture reagent in place of the biotinylated anti-human Fc antibody. Specifically, various concentrations of the anti-ASGR1 mAb-T2 siRNA conjugate were prepared in sample buffer. Because the interaction of the anti-ASGR1 antibody to the ASGR1 antigen is calcium-dependent, 1 mM $CaCl_2$ was added to all buffer solutions for the assay. The samples were hybridized with digoxigenin-TFO (SEQ ID NO: 1) in hybridization buffer at 52° C. for 1 hour. Separately, a biotin-labeled human ASGR1 protein in blocking buffer was deposited into the wells of a streptavidin-coated microtiter plate and shaken for 30 min. The plate was then washed with wash buffer prior to use.

Figure 8:
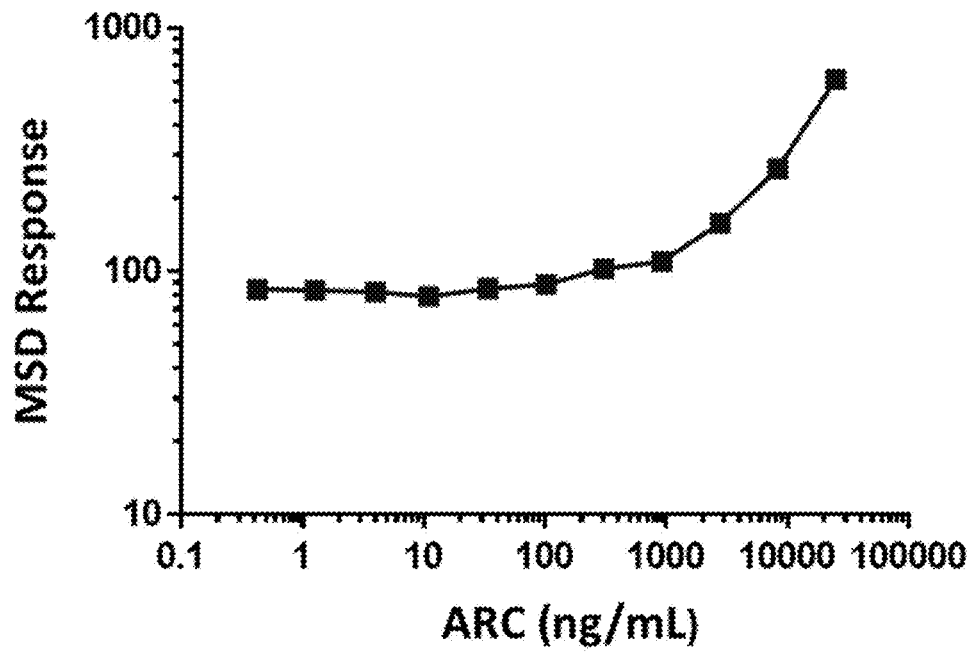
FIG. 8 is a graph showing the relationship between concentration of anti-ASGR1 mAb-siRNA conjugate molecule (ARC) in sample buffer and electro-chemiluminescent signal in arbitrary units (MSD response). The ARC was captured and immobilized to a streptavidin-coated microtiter plate using a biotinylated human ASGR1 protein. A digoxigenin-labeled TFO was used in the assay to hybridize to the siRNA component of the conjugate molecules and enable detection via a ruthenium-labeled anti-digoxigenin antibody.

Following hybridization, the samples were transferred to the previously prepared microtiter plate containing bound human ASGR1 protein and shaken for 1 hour. After washing the plate with wash buffer, a ruthenium-labeled sheep anti-digoxigenin antibody was added to each of the samples in blocking buffer and the plate was shaken for 30 minutes. The plate was again washed with wash buffer and the signal from the ruthenium label was read using a MSD QuickPlex SQ 120 electro-chemiluminescent reader and MSD Read Buffer T with surfactant. The results of the assay are shown in FIG. 8. The LLOQ for the assay was 103 ng/mL. The results demonstrate that the ASGR1 antigen can effectively act as a capture reagent for the conjugate, which can subsequently be detected using the digoxigenin TFO in combination with the ruthenium-labeled anti-digoxigenin antibody.

The results of the experiments described in the example demonstrate that a tagged TFO can be used to enable detection and quantitation of intact antibody-siRNA conjugates in sample solutions in combination with a capture reagent that specifically recognizes the antibody component of the conjugate (e.g. target antigen or anti-Fc antibody).

Example 3. Application of Assay in Pharmacokinetic Analysis in Mice

To demonstrate one of the potential applications of the assay methods of the invention, the assay described in Example 1 and depicted in FIG. 1 (tagged TFO used for capture), was used to analyze serum and liver samples from animals treated with an anti-ASGR1 mAb-siRNA conjugate.

Nine-week old C57Bl/6 wild-type mice were injected subcutaneously or intravenously with the anti-ASGR1 mAb-T2 siRNA conjugate molecule described in Example 1 (30 mg/kg or 60 mg/kg) or a GalNAc-conjugated T2 siRNA control. The GalNAc-conjugated T2 siRNA control was conjugated to a triantennary GalNAc moiety at the 3' end of the sense strand, but otherwise had the same format and sense and antisense strand sequences as the T2 siRNA molecule conjugated to the antibody. The T2 siRNA targets a liver gene. Serum and livers were collected from the animals at days 2, 4, 8, and 15 following compound administration. Total RNA isolated from the livers of the animals was processed for qPCR analysis to assess mRNA levels. Protein expression of the target of the T2 siRNA in the liver was measured by ELISA.

Figure 9A:
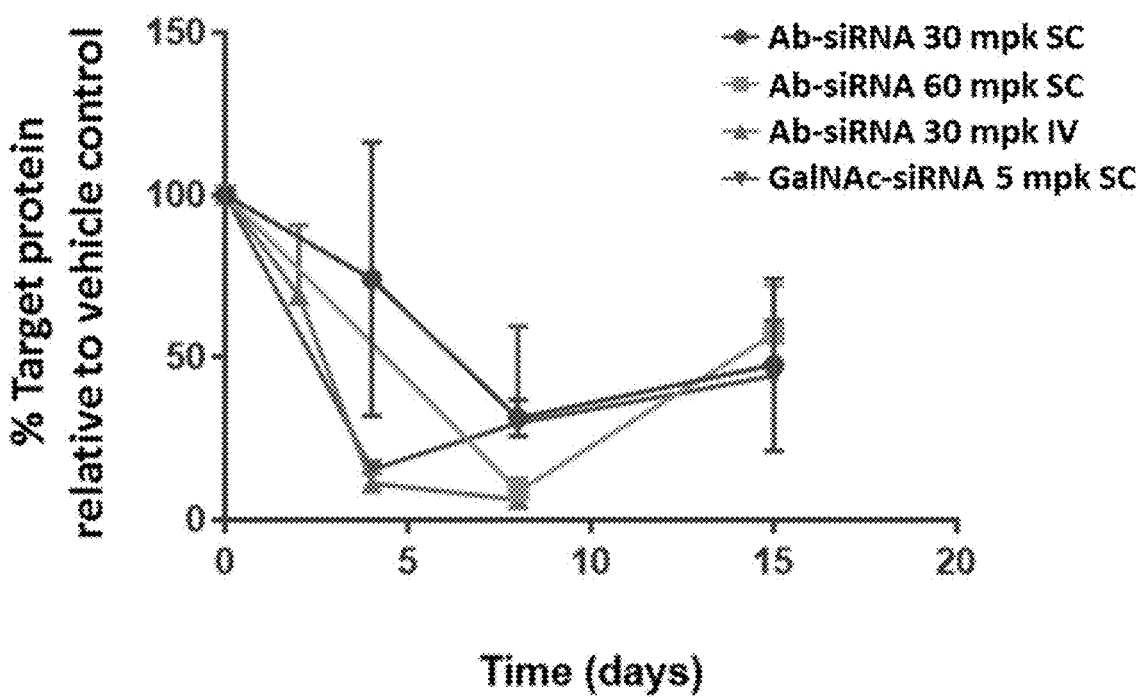
FIG. 9A is a line graph depicting target protein expression in livers from wild-type mice receiving anti-ASGR1 mAb-siRNA conjugate molecule subcutaneously (SC) or intravenously (IV) in all dosing groups measured at the indicated time points (days 2, 4, 8, and 15). The same siRNA conjugated to a GalNAc moiety (GalNAc-siRNA) was used as a positive control. The amount of siRNA in 5 mpk of GalNAc-siRNA is equivalent to that in 30 mpk of the anti-ASGR1 mAb-siRNA conjugate, which has 2 siRNAs/mAb.

The anti-ASGR1 mAb-T2 siRNA conjugate effectively delivered siRNA to its liver target in vivo as shown by the effective reduction in target protein expression in liver (FIG. 9A). A >80% reduction in target protein was achieved in the 30 mpk i.v. group. Nadir of protein knockdown was day 8 for the anti-ASGR1 mAb-T2 siRNA conjugate, dosed either i.v. or s.c., and day 4 for the GalNAc-T2 siRNA conjugate.

The assay method described in Example 1 was used to measure the amount of intact anti-ASGR1 mAb-T2 siRNA conjugate molecules in the serum and liver samples collected from the animals treated with the conjugate. The samples were hybridized with 100 nM biotinylated-TFO (SEQ ID NO: 1) in hybridization buffer at 52° C. for 1 hour. Following hybridization, the samples were transferred to streptavidin-coated plates and washed and blocked as described in Example 1. Detection of the captured conjugate molecules was achieved using the ruthenium-labeled anti-human Fc mAb and the electro-chemiluminescent signal was read by an MSD QuickPlex SQ 120 electro-chemiluminescent reader. As a measure of total drug in the serum and liver samples, an anti-Fc/anti-Fc sandwich ELISA assay was employed. In the total drug ELISA assay, a first biotinylated anti-human Fc antibody was used to capture any anti-ASGR1 mAb in the sample and a second ruthenium-labeled anti-human Fc antibody binding to a different epitope than the first anti-human Fc antibody was used to detect captured anti-ASGR1 mAb. The total drug assay will detect naked anti-ASGR1 mAbs (i.e. mAbs that have lost the siRNA molecules) as well as anti-ASGR1 mAbs with one or two linked siRNA molecules.

Figure 9B:
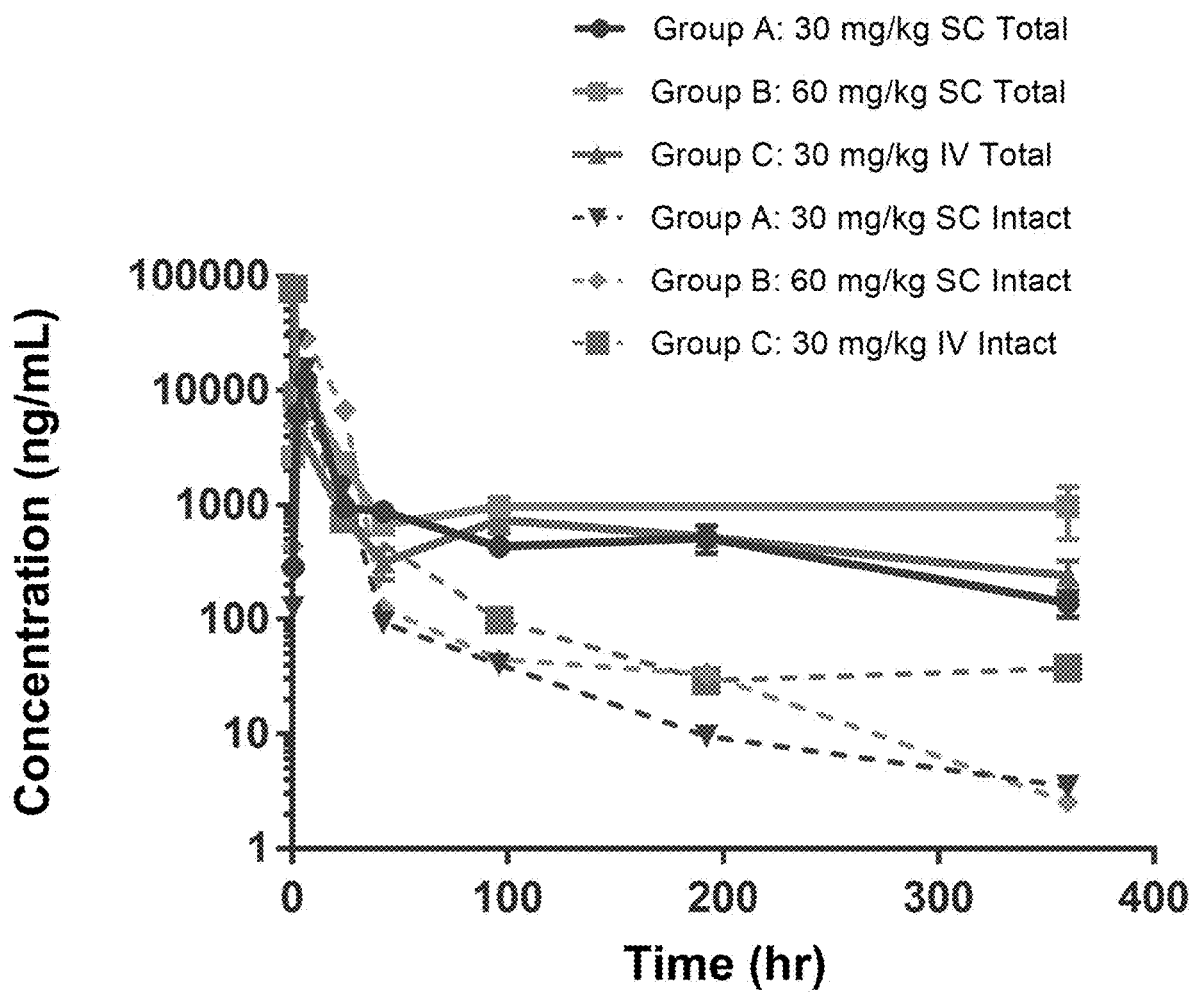
FIG. 9B is a line graph of the relationship between serum concentration of total drug ("Total") or intact anti-ASGR1 mAb-siRNA conjugate molecule ("Intact") over time in mice receiving anti-ASGR1 mAb-siRNA conjugate molecule subcutaneously (SC) or intravenously (IV) at the indicated doses. Serum samples were taken at 2, 4, 8, and 15 days after administration of the conjugate molecules.
Figure 9C:
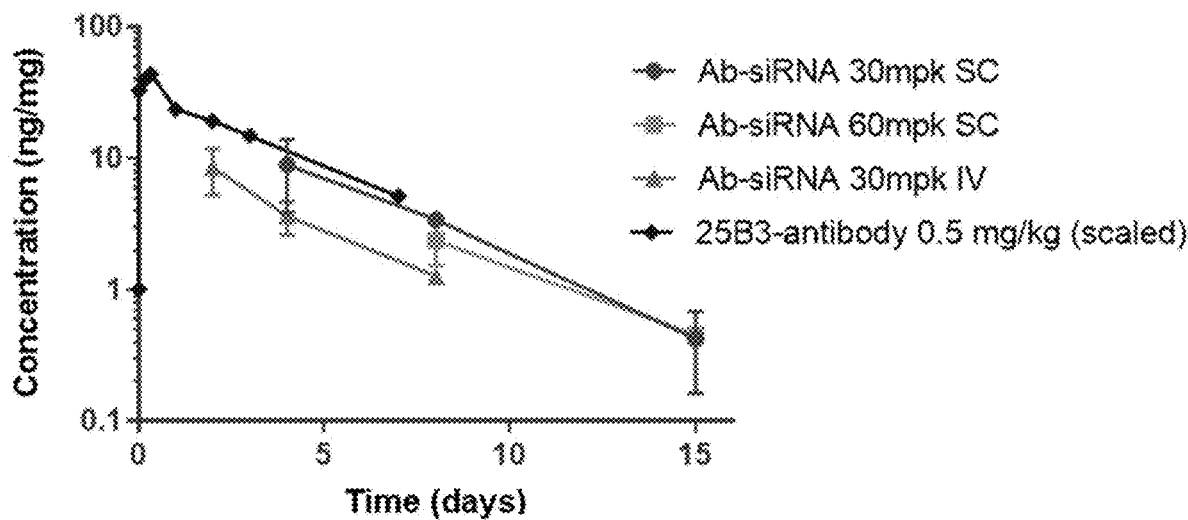
FIG. 9C is a line graph of the relationship between liver concentration of total drug over time in mice receiving anti-ASGR1 mAb-siRNA conjugate molecule subcutaneously (SC) or intravenously (IV) at the indicated doses. Liver samples were taken at 2, 4, 8, and 15 days after administration of the conjugate molecules. Total drug was assessed using an anti-human Fc/anti-human Fc ELISA that detects the anti-ASGR1 mAb component of the conjugates. A dose-adjusted liver concentration of the unconjugated anti-ASGR1 mAb (25B3 antibody) is shown for comparison.
Figure 9D:
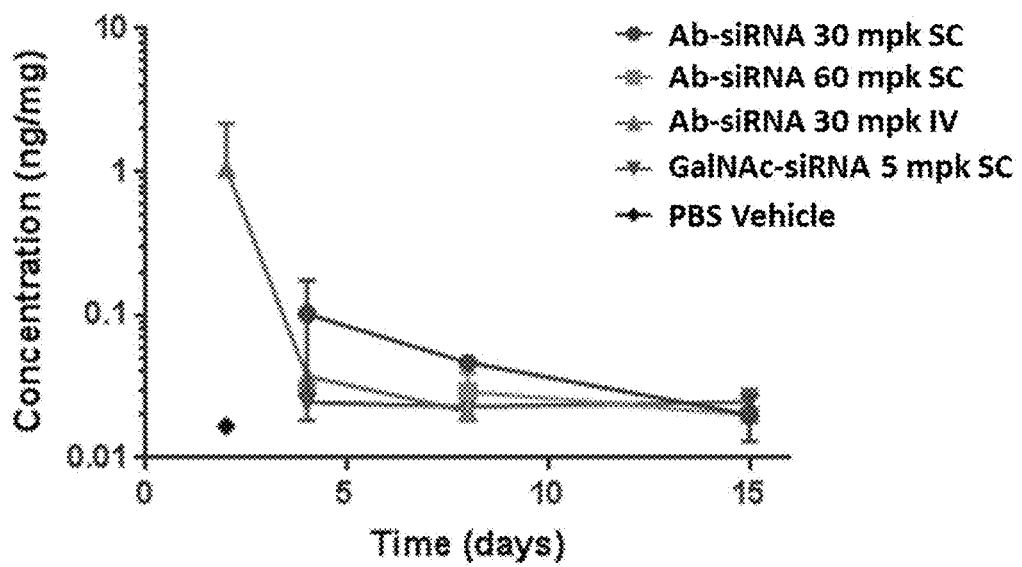
FIG. 9D is a line graph of the relationship between liver concentration of intact drug over time in mice receiving anti-ASGR1 mAb-siRNA conjugate molecule subcutaneously (SC) or intravenously (IV) at the indicated doses. Intact drug was assessed using the assay format depicted in FIG. 1. Liver samples were taken at 2, 4, 8, and 15 days after administration of the conjugate molecules. The liver concentration of the same siRNA conjugated to a GalNAc moiety (GalNAc-siRNA) is shown for comparison.

The results from the analysis of the serum samples are shown in FIG. 9B and the results from the analysis of the liver samples are shown in FIGS. 9C and 9D. The analysis of the serum samples shows a fast serum clearance for the anti-ASGR1 mAb-T2 siRNA conjugate molecules over the first 72 hours, which likely represents a target-mediated ASGR1 clearance pathway. A comparison of the clearance profiles for total drug and the intact conjugates shows that the anti-ASGR1 mAb-T2 siRNA conjugate molecules remain intact (at least one siRNA molecule linked to mAb) over the first 72 hours in serum. The total amount of anti-ASGR1 mAb present in the liver samples as assessed by the total drug ELISA assay shows that conjugation of the siRNA molecule to the antibody does not appear to affect internalization of the antibody as the amounts of the antibody were similar in mice receiving the anti-ASGR1 mAb-siRNA conjugates and the unconjugated anti-ASGR1 mAb (FIG. 9C). The assay method of the invention was able to detect intact anti-ASGR1 mAb-siRNA conjugates in liver tissue of mice that were systemically administered the conjugates (FIG. 9D). The liver concentrations of the intact conjugate molecules were lower than those measured for the total drug (i.e. assessed by anti-ASGR1 mAb concentrations), indicating specific removal of the siRNA molecule in liver tissue.

The experimental results in this example demonstrate that the assay methods of the invention can be employed in pharmacokinetic and drug metabolism studies to assess the clearance profile and metabolic degradation of antibody-siRNA conjugate molecules in vivo.

Example 4. Detection of Triplex Formation

To confirm that the tagged TFO was able to form a triplex with the double-stranded siRNA molecule conjugated to the monoclonal antibody under the hybridization conditions of the assay methods, a native mass spectrometric (native MS) analysis was performed following hybridization of the tagged TFO with the antibody-siRNA conjugate molecule. Specifically, a 168 µM stock solution of the TFO was prepared from lyophilized powder in reaction buffer, which was a 1:1 mixture of sample buffer (10 mM Tris-HCl, 1 mM EDTA, pH 8.0) and hybridization buffer (60 mM sodium phosphate dibasic, 1 M NaCl, 5 mM EDTA, 0.2% (v/v) Tween 20, pH 7.0). The sequence of the TFO was: 5'-AAA CTT CAT CTT TCT TCC CAC-3' (SEQ ID NO: 1; LNA monomers are indicated by underlining and bold font), and was labeled at the 3' end with biotin. The approximate molecular weight of the biotinylated TFO was 6856.6 Daltons. The biotinylated TFO was mixed 1:1 v/v with a 2.4 mg/mL stock solution of the anti-ASGR1 mAb-T2 siRNA conjugate molecule described in Example 1. A conjugate molecule with RNA-to-antibody ratio (RAR) of 1 was used for this experiment. The final concentrations of the biotinylated TFO and the anti-ASGR1 mAb-T2 siRNA RAR1 conjugate molecule were 84 µM and ~7.5 µM, respectively. The mixture was incubated at 52° C. for 1 h and cooled to 12° C. until further analysis.

Prior to native-MS analysis, the sample was buffer exchanged into 200 mM ammonium acetate using a P6 spin column (BioRad, 732-6221) and was introduced into the mass spectrometer using nESI gold coated glass needles (long thin wall, M956232AD1-S; Waters Corporation). The native-MS experiments were performed using the Synapt G1 Q-ToF instrument (Waters Corporation) in positive ionization mode. Mild collisional activation was performed in source (Sample Cone, 50 V) and the collision cell (pressurized with cC4F8) set to a voltage of 20 to 30 V. The mass spectrometer was externally calibrated with cesium iodide over the m/z range 100 to 20,000.

Figure 10A:
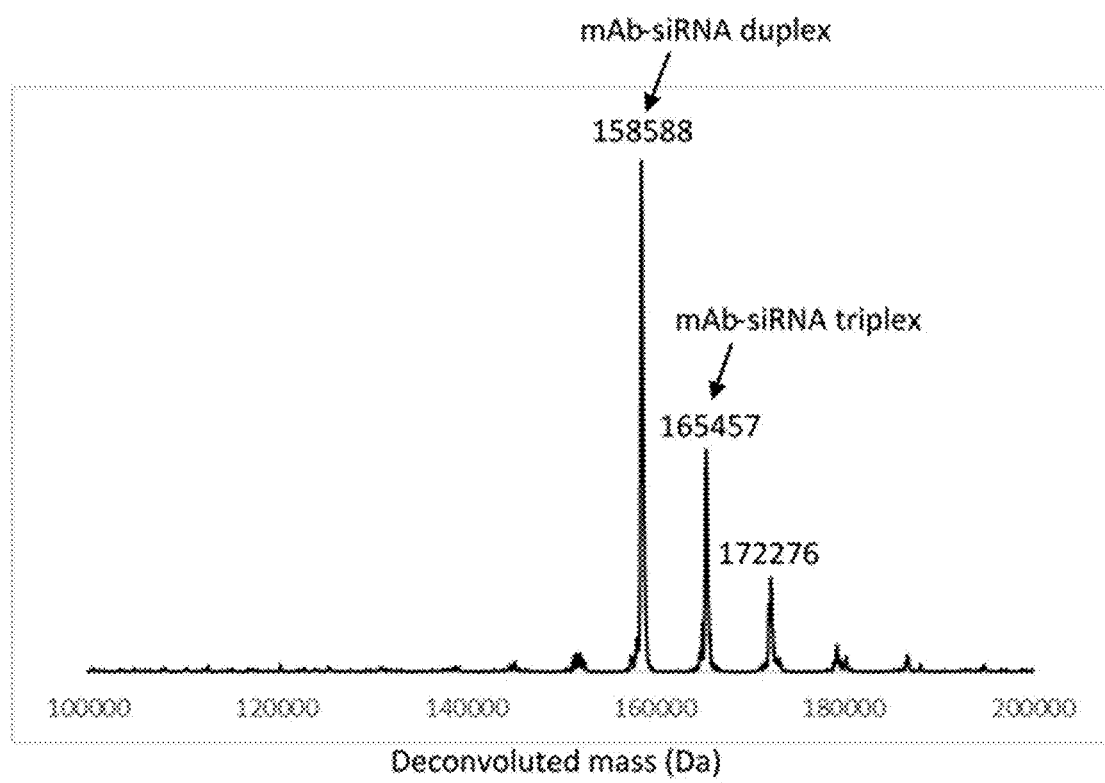
FIG. 10A is native mass spectrum of the hybridization mixture of a monoclonal antibody-siRNA conjugate molecule and a biotinylated TFO. The siRNA molecule was conjugated to the antibody at an RNA-to-antibody ratio of 1 (RAR1). The mAb-siRNA RAR1 conjugate molecule was hybridized with the biotinylated TFO for 1 hour at 52° C. A peak is observed at 165 kDa, which corresponds to a conjugate molecule in which the biotinylated TFO is hybridized to the siRNA component of the conjugate molecule to form a triplex (mAb-siRNA triplex).
Figure 10B:
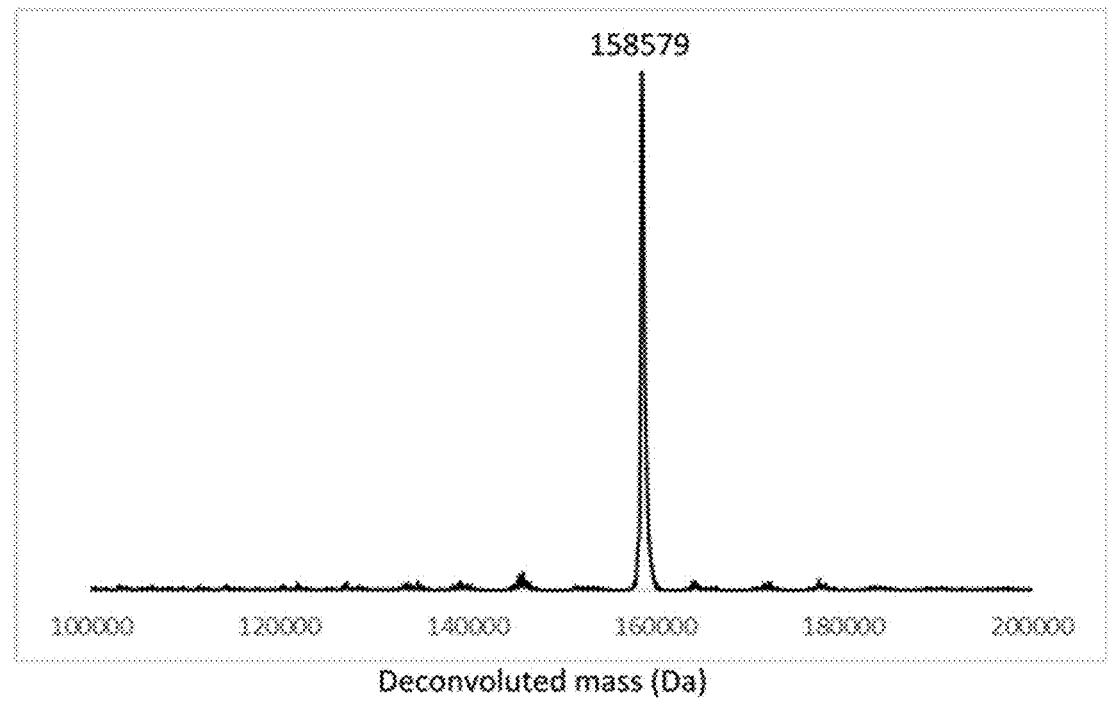
FIG. 10B is native mass spectrum of the mAb-siRNA RAR1 conjugate molecule in FIG. 10A in the absence of the biotinylated TFO. Only a peak at 158 kDa is observed, corresponding to the expected molecular weight of the monoclonal antibody with one siRNA molecule covalently attached.

The results of the native MS analysis are shown in FIG. 10. A species with a molecular weight consistent with a mAb-siRNA triplex (i.e. a biotinylated TFO hybridized to the siRNA component of the conjugate molecule) was observed following incubation with the biotinylated TFO. See FIG. 10A. The mAb-siRNA triplex peak is not observed when the anti-ASGR1 mAb-T2 siRNA RAR1 conjugate molecule is not exposed to the biotinylated TFO. See FIG.

10B. The results of this experiment demonstrate that the biotinylated TFO is able to form a triplex with the siRNA component of an antibody-siRNA conjugate molecule under the hybridization conditions of the assay methods described herein.

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. An assay system for detecting a protein-polynucleotide conjugate molecule in a sample, comprising:
   (a) a triplex forming oligonucleotide (TFO) that is covalently linked to a tag, wherein the TFO is capable of hybridizing to the polynucleotide in the conjugate molecule;
   (b) a surface comprising a capture reagent that specifically binds to the tag covalently linked to the TFO; and
   (c) a detection reagent comprising a detectable label coupled to a binding partner that specifically binds to the protein in the conjugate molecule.

2. The assay system of claim 1, wherein the tag is a hapten.

3. The assay system of claim 2, wherein the hapten is biotin, digoxigenin, or 2,4-dinitrophenol.

4. The assay system of claim 1, wherein the TFO is at least 15 nucleotides in length.

5. The assay system of claim 1, wherein the TFO is about 15 nucleotides to about 30 nucleotides in length.

6. The assay system of claim 1, wherein the TFO comprises a mixture of locked nucleic acid (LNA) monomers and deoxyribonucleotides.

7. The assay system of claim 6, wherein about 30% to about 40% of the nucleotides in the TFO are LNA monomers.

8. The assay system of claim 1, wherein the TFO has a sequence that is complementary to the sequence of the polynucleotide in the conjugate molecule over its entire length.

9. The assay system of claim 1, wherein the capture reagent is an antibody that specifically binds to the tag.

10. The assay system of claim 1, wherein the tag is biotin and the capture reagent is streptavidin.

11. The assay system of claim 1, wherein the tag is digoxigenin and the capture reagent is an antibody that specifically binds to digoxigenin.

12. The assay system of claim 1, wherein the surface is a bead, a particle, a membrane, a resin, a column, an electrode, or a well in a microtiter plate.

13. The assay system of claim 1, wherein the binding partner in the detection reagent is an antibody that specifically binds to the protein in the conjugate molecule.

14. The assay system of claim 1, wherein the detectable label in the detection reagent is a fluorophore, metallic nanoparticle, enzyme, or electrochemiluminescence (ECL) luminophore.

15. The assay system of claim 14, wherein the ECL luminophore is a ruthenium complex.

16. The assay system of claim 1, wherein the protein-polynucleotide conjugate molecule is an antibody-siRNA conjugate molecule.

17. The assay system of claim 16, wherein the siRNA comprises a sense strand and an antisense strand, and wherein the TFO has a sequence that is complementary to the sequence of the sense strand.

18. The assay system of claim 16, wherein the binding partner in the detection reagent is a target antigen of the antibody, an anti-Fc region antibody, or an anti-idiotypic antibody.

19. An assay system for detecting a protein-polynucleotide conjugate molecule in a sample, comprising:
   (a) a TFO that is covalently linked to a tag, wherein the TFO is capable of hybridizing to the polynucleotide in the conjugate molecule;
   (b) a surface comprising a capture reagent that specifically binds to the protein in the conjugate molecule; and
   (c) a detection reagent comprising a detectable label coupled to a binding partner that specifically binds to the tag covalently linked to the TFO.

20. The assay system of claim 19, wherein the tag is a hapten.

21. The assay system of claim 20, wherein the hapten is biotin, digoxigenin, or 2,4-dinitrophenol.

22. The assay system of claim 19, wherein the TFO is at least 15 nucleotides in length.

23. The assay system of claim 19, wherein the TFO is about 15 nucleotides to about 30 nucleotides in length.

24. The assay system of claim 19, wherein the TFO comprises a mixture of locked nucleic acid (LNA) monomers and deoxyribonucleotides.

25. The assay system of claim 24, wherein about 30% to about 40% of the nucleotides in the TFO are LNA monomers.

26. The assay system of claim 19, wherein the TFO has a sequence that is complementary to the sequence of the polynucleotide in the conjugate molecule over its entire length.

27. The assay system of claim 19, wherein the capture reagent is an antibody that specifically binds to the protein in the conjugate molecule.

28. The assay system of claim 19, wherein the surface is a bead, a particle, a membrane, a resin, a column, an electrode, or a well in a microtiter plate.

29. The assay system of claim 19, wherein the binding partner in the detection reagent is an antibody that specifically binds to the tag.

30. The assay system of claim 19, wherein the tag is biotin and the binding partner in the detection reagent is streptavidin.

31. The assay system of claim 19, wherein the tag is digoxigenin and the binding partner in the detection reagent is an antibody that specifically binds to digoxigenin.

32. The assay system of claim 19, wherein the detectable label in the detection reagent is a fluorophore, metallic nanoparticle, enzyme, or electrochemiluminescence (ECL) luminophore.

33. The assay system of claim 32, wherein the ECL luminophore is a ruthenium complex.

34. The assay system of claim 19, wherein the protein-polynucleotide conjugate molecule is an antibody-siRNA conjugate molecule.

35. The assay system of claim 34, wherein the siRNA comprises a sense strand and an antisense strand, and wherein the TFO has a sequence that is complementary to the sequence of the sense strand.

36. The assay system of claim 34, wherein the capture reagent is a target antigen of the antibody, an anti-Fc region antibody, an anti-idiotypic antibody, protein A, or protein G.

37. A method for detecting antibody-polynucleotide conjugate molecules in a biological sample comprising:
(a) contacting the sample with a TFO that is covalently linked to a tag under conditions that allow the TFO to hybridize to the polynucleotide in the conjugate molecule, thereby forming a hybridization mixture;
(b) contacting the hybridization mixture with a surface comprising a capture reagent that specifically binds to the tag covalently linked to the TFO;
(c) contacting the surface with a detection reagent, wherein the detection reagent comprises a detectable label coupled to a binding partner that specifically binds to the antibody in the conjugate molecule; and
(d) detecting a signal from the detectable label.

\* \* \* \* \*